United States Patent
Tammana et al.

(10) Patent No.: US 10,927,059 B2
(45) Date of Patent: Feb. 23, 2021

(54) CATALYST FOR CONVERTING HEAVY REFORMATE TO PRODUCE BTX COMPOUNDS

(71) Applicants: Saudi Arabian Oil Company, Dhahran (SA); Instituto de Tecnologia Quimica, UPV-CSIC, Valencia (ES)

(72) Inventors: Veera Venkata Ramakrishna Tammana, Ras Tanura (SA); Raed Abudawoud, Al-Khobar (SA); Avelino Corma Canos, Valencia (ES); M. Teresa Portilla Ovejero, Valencia (ES); M. Cristina Martinez Sanchez, Valencia (ES); Ibrahim M. Al-Zahrani, Dammam (SA)

(73) Assignees: Saudi Arabian Oil Company, Dhahran (SA); Universitat Politecnica De Valencia, Valencia (ES); Consejo Superior De Investigaciones Cientificas, Madrid (ES)

( * ) Notice: Subject to any disclaimer, the term of this patent is extended or adjusted under 35 U.S.C. 154(b) by 0 days.

(21) Appl. No.: 16/299,838

(22) Filed: Mar. 12, 2019

(65) Prior Publication Data
US 2019/0284115 A1    Sep. 19, 2019

(30) Foreign Application Priority Data
Mar. 14, 2018 (EP) .................................... 18382169

(51) Int. Cl.
*C07C 6/12* (2006.01)
*B01J 29/46* (2006.01)
(Continued)

(52) U.S. Cl.
CPC ............. *C07C 6/126* (2013.01); *B01J 29/045* (2013.01); *B01J 29/22* (2013.01); *B01J 29/24* (2013.01);
(Continued)

(58) Field of Classification Search
None
See application file for complete search history.

(56) References Cited

U.S. PATENT DOCUMENTS

| 4,467,129 A | 8/1984 | Iwayama et al. |
| 4,963,337 A | 10/1990 | Zones |

(Continued)

FOREIGN PATENT DOCUMENTS

| CN | 101121132 A | 2/2008 |
| CN | 101121137 A | 2/2008 |

(Continued)

OTHER PUBLICATIONS

International Search Report and Written Opinion dated Jun. 27, 2019 pertaining to International application No. PCT/US2019/021592 filed Mar. 11, 2019, 15 pgs.

(Continued)

*Primary Examiner* — Philip Y Louie
*Assistant Examiner* — Alyssa L Cepluch
(74) *Attorney, Agent, or Firm* — Dinsmore & Shohl LLP

(57) ABSTRACT

A method of making BTX (benzene, toluene, xylene) compounds by feeding a heavy reformate stream to a reactor, where the reactor includes a composite zeolite catalyst, that contains a mixture of a desilicated mesoporous mordenite and ZSM-5, and in which the desilicated mesoporous mordenite, the ZSM-5, or both, comprise one or more impregnated metals. The composite zeolite catalyst is able to catalyze the transalkylation reaction and the dealkylation reaction simultaneously to produce the BTX compounds.

13 Claims, 18 Drawing Sheets

(51) Int. Cl.

| | |
|---|---|
| *B01J 29/80* | (2006.01) |
| *B01J 29/26* | (2006.01) |
| *B01J 29/04* | (2006.01) |
| *B01J 29/48* | (2006.01) |
| *B01J 35/10* | (2006.01) |
| *C07C 4/18* | (2006.01) |
| *B01J 29/44* | (2006.01) |
| *B01J 35/00* | (2006.01) |
| *B01J 29/24* | (2006.01) |
| *B01J 29/22* | (2006.01) |
| *B01J 29/06* | (2006.01) |
| *C07C 15/04* | (2006.01) |
| *C07C 15/06* | (2006.01) |
| *C07C 15/08* | (2006.01) |

(52) U.S. Cl.
CPC ............ *B01J 29/26* (2013.01); *B01J 29/44* (2013.01); *B01J 29/46* (2013.01); *B01J 29/48* (2013.01); *B01J 29/80* (2013.01); *B01J 35/002* (2013.01); *B01J 35/1004* (2013.01); *B01J 35/1019* (2013.01); *B01J 35/1061* (2013.01); *C07C 4/18* (2013.01); *B01J 35/1038* (2013.01); *B01J 2029/062* (2013.01); *B01J 2229/10* (2013.01); *B01J 2229/16* (2013.01); *B01J 2229/186* (2013.01); *C07C 15/04* (2013.01); *C07C 15/06* (2013.01); *C07C 15/08* (2013.01); *C07C 2529/24* (2013.01); *C07C 2529/46* (2013.01)

(56) References Cited

U.S. PATENT DOCUMENTS

| | | | |
|---|---|---|---|
| 5,043,513 | A | 8/1991 | Howley et al. |
| 5,120,425 | A | 6/1992 | Zones et al. |
| 5,865,986 | A | 2/1999 | Buchanan et al. |
| 5,942,651 | A | 8/1999 | Beech, Jr. et al. |
| 5,952,536 | A | 9/1999 | Nacamuli et al. |
| 7,393,989 | B2 | 7/2008 | Negiz et al. |
| 8,242,321 | B2 | 8/2012 | Boldingh et al. |
| 8,329,973 | B2 | 12/2012 | Inui et al. |
| 8,653,315 | B2 | 2/2014 | Ali |
| 9,242,236 | B2 | 1/2016 | Xie et al. |
| 2002/0092797 | A1 | 7/2002 | Choi et al. |
| 2005/0234279 | A1 | 10/2005 | Serra et al. |
| 2009/0023968 | A1 | 1/2009 | Wang et al. |
| 2009/0112034 | A1 | 4/2009 | Levin |
| 2009/0325785 | A1 | 12/2009 | Moscoso et al. |
| 2010/0029467 | A1 | 2/2010 | Inui et al. |
| 2011/0127193 | A1 | 6/2011 | Xie et al. |
| 2012/0027673 | A1 | 2/2012 | Larsen et al. |
| 2012/0083635 | A1 | 4/2012 | Boldingh et al. |
| 2012/0165558 | A1 | 6/2012 | Ryoo et al. |
| 2012/0258852 | A1* | 10/2012 | Martinez ............... B01J 29/041 502/60 |
| 2013/0261365 | A1 | 10/2013 | Wang et al. |
| 2013/0281750 | A1* | 10/2013 | Abudawoud ............ C07C 6/06 585/321 |
| 2018/0134637 | A1 | 5/2018 | Lai et al. |

FOREIGN PATENT DOCUMENTS

| | | |
|---|---|---|
| CN | 101190418 A | 6/2008 |
| CN | 101190864 A | 6/2008 |
| CN | 101191069 A | 6/2008 |
| CN | 101347746 A | 1/2009 |
| CN | 101348407 A | 1/2009 |
| CN | 101602639 A | 12/2009 |
| CN | 101885663 A | 11/2010 |
| CN | 101811063 B | 10/2012 |
| CN | 104437611 A | 3/2015 |
| CN | 104437613 A | 3/2015 |
| EP | 042754 A1 | 6/1981 |
| EP | 109962 A1 | 6/1984 |
| EP | 1586376 A1 | 10/2005 |
| EP | 1775277 A1 | 4/2007 |
| WO | 2004046278 A1 | 6/2004 |
| WO | 2005118515 A1 | 12/2005 |
| WO | 2010150996 A2 | 12/2010 |
| WO | 2018011122 A1 | 1/2018 |
| WO | 2018071184 A1 | 4/2018 |
| WO | 2018231340 A1 | 12/2018 |

OTHER PUBLICATIONS

International Search Report and Written Opinion dated Jun. 28, 2019 pertaining to International application No. PCT/US2019/021597 filed Mar. 11, 2019, 17 pgs.

International Search Report and Written Opinion dated Jun. 26, 2019 pertaining to International application No. PCT/US2019/021590 filed Mar. 11, 2019, 23 pgs.

International Search Report and Written Opinion dated Jun. 26, 2019 pertaining to International application No. PCT/US2019/021595 filed Mar. 11, 2019, 20 pgs.

Ali et al., "Selective production of xylenes from alkyl-aromatics and heavy reformates over dual-zeolite catalyst", Catalysis Today, vol. 243, pp. 118-127 (2015).

Al-Khattaf et al., "Catalytic transformation of methyl benzenes over zeolite catalysts", Applied Catalysis A: General 394, pp. 176-190, 2011.

Calderia et al., "Properties of hierarchical Beta zeolites prepared from protozeolitic nanounits for the catalytic cracking of high density polyethylene", Applied Catalysts A: General 531, pp. 187-196, 2017.

Choi et al., "Stable single-unit-cell nanosheets of zeolite MFI as active and long-lived catalysts", Nature, vol. 461, pp. 246-250, Sep. 10, 2009.

Corma et al., "Discovery of new paraffin isomerization catalysts based on SO4 2-/ZrO2 and Wox/ZrO2 applying combinatorial techniques", Catalysts Today 81, pp. 495-506, 2003.

Han et al., Zeolite Synthesis Using Flexible Diquarternary Alkylammonium Ions (CnH2n+1)2HN+(CH2)5N+H(CnH2n+1)2 with n=1-5 as Structure-Directing Agents, Chem Mater, vol. 17, pp. 477-486, 2005.

Jackowski et al., "Diquaternary Ammonium Compounds in Zeolite Synthesis: Cyclic and Polycyclic N-Heterocycles Connected by Methylene Chains", American Chemical Society, 131, 1092-1100 (2009).

Jo et al., "Capping with Multivalent Surfactants for Zeolite Nanocrystal Synthesis", Angew. Chem, vol. 125, pp. 10198-10201, 2013 with Supporting Information.

Kim et al., "Bulk crystal seeing on generation of mesoporoes by organosilane surfactants in zeolite synthesis", Electronic Supplementary (ESI) for Journal of Masterials Chemistry A., The Royal Society of Chemistry 2014.

Kong et al., "Fabrication of core/shell structure via overgrowth of ZSM-5 layers on mordenite cyrstals", Microporous and Mesoporous Materials, vol. 119, pp. 91-96, 2009.

Konysheva et al., "Effect of Nature of Heteroelement (Ba, Ga, Al) on Adsorption of Acid Characteristics of Hierarchical Porous Zeolites of MOR, BEA and MTW Strucural Types", Theoretical and Experimental Chemistry, vol. 53, No. 6, pp. 410-416, Jan. 2018.

Va Laak et al., "Mesoporous mordenites obtained by sequential acid and alkaline treatments—Catalysts for cumene production with enhanced accessibility", Journal of Catalysis, vol. 276, pp. 170-180, 2010.

Lee et al., "Reinvestigation into the synthesis of zeolites using diquaternary alkylammonium ions (CH3)3N+(CH2)nN+(CH3)3 with n=3-10 as structure-directing agents", Microporous and Mesoporous Materials, vol. 68, pp. 97-104, 2004.

Lee et al., "Zeolite synthesis in the presence of flexible diquaternary alkylammonium ions (C2H5)3N+(CH2)nN+(C2H5)3 with n+3-10 as structure-directing agents", Microporous and Mesoporous Materials, vol. 60, pp. 237-249, 2003.

(56) References Cited

OTHER PUBLICATIONS

Li et al., "One-pot synthesis of hierarchical mordenite and its performance in the benzylation of benzene with benzyl alcohol", J. Matter Sci, vol. 50, pp. 5059-5067, 2015.
Mihayli et al., "Transformation of ethylbenzene-m-xylene misture on zeolites with different structures", J. Porous Matter, vol. 21, pp. 485-493, 2014.
Liu et al., "Catalytic Properties of Hierarchical Mordenite Nanosheets Synthesized by Self-Assembly Between Subnanocrystals and Organic Templates", Catal Lett, vol. 146, pp. 249-254, 2016 with Electronic Supplementary Information.
Moller et al., "Mesoporosity—a new dimension for Zeolites", Chem Soc Rev. vol. 42, pp. 3689-3707, 2013.
Ordomsky et al., "Cumene disproportionation over micro/mesoprous catalysts obtained by recrystallization of mordenite", Journal of Catalysis, vol. 295, pp. 207-216, 2012.
Shvets et al., "New Approaches to Creation of Micro- and Mesoporous Functional Materials", Theoretical and Experimental Chemiustry, vol. 53, No. 5, Nov. 2017.
Thommes et al., "Physisorption of gases, with special reference to the evaluation of surface area and pore size distribution (IUPAC Technical Report)", Pure Appl. Chem., 87(9-10), pp. 1051-1069, 2015.
Verboekend et al., "Design of hierarchical zeolite catalysts by desilication", Catalysis Science & Technology, vol. 1, pp. 879-890, 2011.
Vitvarova et al., "Catalytic applications and FTIR investigation of zeolite SSZ-33 after isomorphous substitution", Microporous and Mesoporous Materials, vol. 194, pp. 174-182, 2014.
Zones et al., "Boron-beta zeolite hydrothermal conversions: the influence of template structure and of boron concentration and source", Microporous Materials, vol. 2, pp. 543-555, 1994.
European Search Report pertaining to European Application No. 18382172.7 dated Jan. 4, 2019.
European Search Report pertaining to European Application No. 18382170.1 dated Sep. 27, 2018.
European Search Report pertaining to European Application No. 18382168.5 dated Sep. 27, 2018.
European Search Report pertaining to European Application No. 18382167.7 dated Jan. 4, 2019.
European Search Report pertaining to European Application No. 18382169.3 dated Sep. 27, 2018.
European Search Report pertaining to European Application No. 18382171.9 dated Oct. 5, 2018.
Galarneau et al., Validity of the t-plot Method to Assess Microporosity in Hierarchical Micro/Mesoporous Materials, Langmuir 2014, 9 pgs.
International Search Report and Written Opinion dated Sep. 20, 2019 pertaining to International application No. PCT/US2019/021594 filed Mar. 11, 2019.
Notice of Allowance and Fee(s) Due dated Apr. 17, 2020 pertaining to U.S. Appl. No. 16/299,832, filed Mar. 12, 2019, 31 pgs.
Notice of Allowance and Fee(s) Due dated Apr. 8, 2020 pertaining to U.S. Appl. No. 16/299,704, filed Mar. 12, 2019, 31 pgs.
Office Action dated Dec. 2, 2019 pertaining to U.S. Appl. No. 16/299,717, filed Mar. 12, 2019, 26 pgs.
Office Action dated Dec. 4, 2019 pertaining to U.S. Appl. No. 16/299,723, filed Mar. 12, 2019, 30 pgs.
Office Action dated Dec. 20, 2019 pertaining to U.S. Appl. No. 16/299,844, filed Mar. 12, 2019, 31 pgs.
Machine translation CN 101811063, Aug. 25, 2010, retrieved Dec. 6, 2019 (Year: 2019).
Camblor et al. "Characterization of Nanocrystalline Zeolite Beta" Microporous and Mesoporous Materials 25 (1998) pp. 59-74 (Year: 1998).
Office Action dated Jun. 12, 2020 pertaining to U.S. Appl. No. 16/299,723, filed Mar. 12, 2019, 18 pgs.
Dai et al. "Hierarchical mordenite zeolite nano-rods bundles favourable to bulky molecules" Chemical Physics Letters 686 (2017) 111-115 (Year: 2017).
Office Action dated Jun. 29, 2020 pertaining to U.S. Appl. No. 16/299,844, filed Mar. 12, 2019, 23 pgs.
Office Action dated Oct. 5, 2020 pertaining to U.S. Appl. No. 16/299,723, filed Mar. 12, 2019, 10 pgs.
Sharma et al. "Synthesis and morphological studies of nanocrystalline MOR type zeolite material" Journal of Colloid and Interface Science, 2008 325, 547-557. (Year: 2008).
Office Action dated Oct. 14, 2020 pertaining to U.S. Appl. No. 16/299,844, filed Mar. 12, 2019, 15 pgs.

* cited by examiner

US 10,927,059 B2

CATALYST FOR CONVERTING HEAVY REFORMATE TO PRODUCE BTX COMPOUNDS

CROSS REFERENCE TO RELATED APPLICATIONS

This application claims priority to European Patent Application No. 18382169.3, filed Mar. 14, 2018 which is hereby incorporated by reference in its entirety.

TECHNICAL FIELD

Embodiments of the present specification generally relate to methods of producing BTX (benzene, toluene, and xylene) compounds, and specifically relate to methods of using a composite zeolite catalyst to upgrade heavy reformate fractions into BTX compounds.

BACKGROUND

In petroleum upgrading systems, after BTEX (benzene, toluene, ethylbenzene, and xylene) compounds are extracted from catalytic reformate or pyrolysis gasoline fractions, the leftover fraction (containing mostly $C_{9+}$ aromatic compounds) is referred to as a heavy reformate (HR) fraction. Historically, the HR fraction would be added directly to a gasoline pool; however, due to increasing stringency in environmental regulations, the HR fraction now requires further upgrading before it is suitable for use.

The HR fraction may be further upgraded to additional BTX compounds by first dealkylating the $C_{9+}$ aromatic compounds to produce toluene, then passing the remaining fraction to a second reactor to undergo transalkylation and produce benzene and xylene. However, these conventional means have limited efficiency because of the sequential nature of the conversion reaction process, in which the products of the first reaction are utilized in a second reaction.

SUMMARY

Accordingly, ongoing needs exist for efficiently and effectively converting heavy reformate fractions into BTX compounds. Embodiments of the present disclosure are related to methods of making BTX compounds by feeding a heavy reformate stream to a reactor containing a composite zeolite catalyst to produce BTX compounds by simultaneously catalyzing transalkylation and dealkylation reactions.

In some embodiments, methods of making BTX compounds comprising benzene, toluene, and xylene are provided. The method includes feeding a heavy reformate stream to a reactor, in which the reactor comprising a composite zeolite catalyst and the composite zeolite catalyst includes a mixture of desilicated mesoporous mordenite and ZSM-5 (Zeolite Socony Mobil-5, described in detail infra). The desilicated mesoporous mordenite, the ZSM-5, or both, comprise one or more impregnated metals. The method further includes producing the BTX compounds by simultaneously performing a transalkylation reaction and a dealkylation reaction of the heavy reformate stream in the reactor, in which the composite zeolite catalyst is able to catalyze both the transalkylation reaction and the dealkylation reaction simultaneously.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Figure 1A:
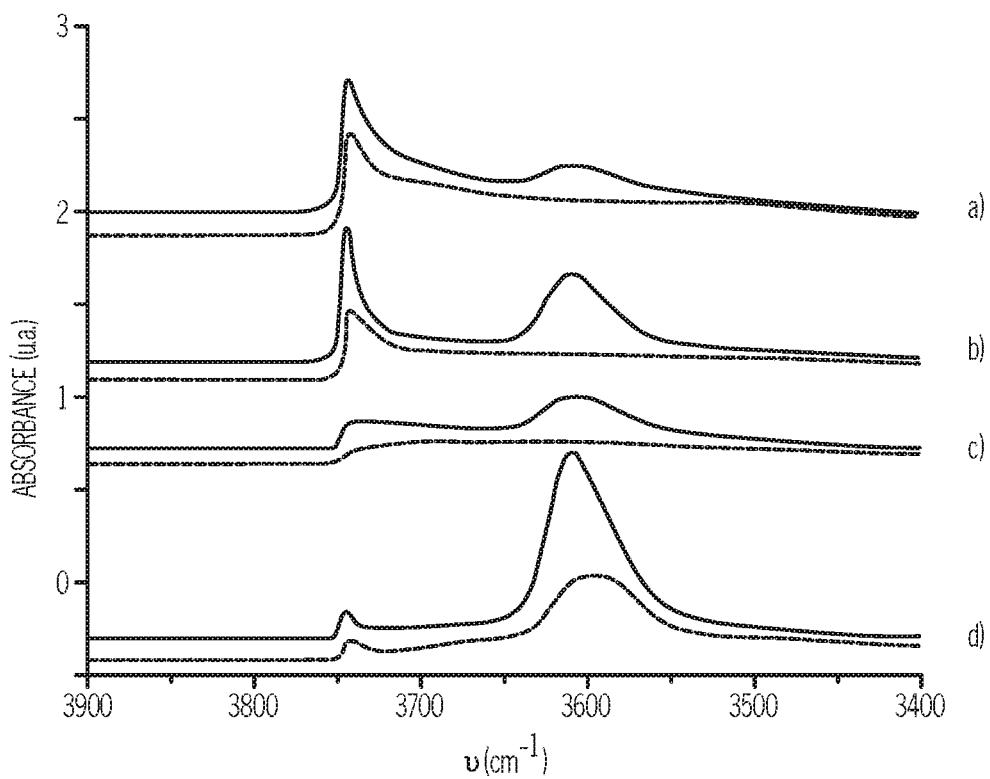
FIG. 1A is a stacked Fourier Transform Infrared (FT-IR) spectra of a hydroxyl region of mordenite samples. The solid lines correspond to the spectra recorded after each mordenite sample was pretreated at 400° C. under vacuum, and the dotted lines correspond to the spectra recorded after pyridine adsorption and desorption at 150° C. The mordenite samples are described in the Example section infra and are as follows: a) Cat. 2, b) Cat. 1, c) MOR-A treated once with nitric acid, and d) MOR.

Specific embodiments of the present application are described within this disclosure. The disclosure may, however, be embodied in different forms and should not be construed as limited to the embodiments set forth. Rather, these embodiments are provided so that this disclosure will be thorough and complete, and will fully convey the scope of the subject matter to those having skill in the art.

Unless otherwise defined, all technical and scientific terms used have the same meaning as commonly understood by one of ordinary skill in the art. The terminology used in this description is for describing particular embodiments only and is not intended to be limiting. As used in the specification and appended claims, the singular forms "a," "an," and "the" are intended to include the plural forms as well, unless the context clearly indicates otherwise. Unless otherwise indicated, the disclosure of any ranges in the specification and claims are to be understood as including the range itself and also anything subsumed within the range, as well as endpoints.

Embodiments of the present disclosure relate to methods of making BTX compounds (compounds containing at least one of benzene, toluene, or xylene) by feeding a heavy reformate stream into a reactor that contains a composite zeolite catalyst. The composite zeolite catalyst contains a mixture of desilicated mesoporous mordenite and ZSM-5 and is able to catalyze both transalkylation and dealkylation reactions simultaneously in the reactor to produce BTX compounds.

The term "heavy reformate (HR) stream," "heavy reformate fraction," or "heavy reformate feed," all refer to a feed stream that includes at least para-methylethylbenzene (p-MEB) and 1,2,4-trimethylbenzene (1,2,4-TMB). The composition of an industrial heavy reformate feed is given in Table 1:

TABLE 1

Industrial Heavy Reformate Composition

| Component | | |
|---|---|---|
| Hydrocarbon Type | Hydrocarbon Sub-Type | Weight % |
| $A_8$ | Total | 3.94 |
| | Ethylbenzene | 0.03 |
| | p-xylene | 0.15 |
| | m-xylene | 0.38 |
| | o-xylene | 3.38 |
| $A_9$ | Total | 82.75 |
| | Isopropylbenzene Total | 0.43 |
| | n-propylbenzene Total | 2.07 |
| | Methylethylbenzene Total | 19.62 |
| | (MEB) m- and p-MEB | 15.33 |
| | o-MEB | 4.29 |

TABLE 1-continued

Industrial Heavy Reformate Composition

| Component | | |
|---|---|---|
| Hydrocarbon Type | Hydrocarbon Sub-Type | Weight % |
| | Trimethylbenzene (TMB) | Total | 60.63 |
| | | 1,3,5-TMB | 11.69 |
| | | 1,2,4-TMB | 40.81 |
| | | 1,2,3-TMB | 8.13 |
| $A_{10+}$ | Total | | 13.33 |

The main components of heavy reformate stream are ethyl-toluenes (methyl-ethyl-benzenes, MEB) and trimethyl-benzenes (TMB). The structures of MEB isomers and TMB isomers are provided infra.

MEB isomers

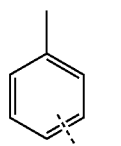

(para, meta and ortho)

TMB isomers

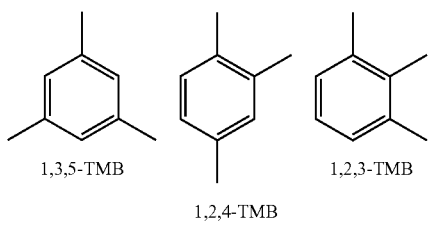

1,3,5-TMB   1,2,4-TMB   1,2,3-TMB

The heavy reformate stream is usually produced as a by-product after BTEX compounds are extracted from catalytic reformate or pyrolysis gas fractions. The remaining heavy carbons, typically $C_{9+}$ aromatics, make up the heavy reformate stream. As mentioned, the main components of the heavy reformate stream are MEB and TMB, and specifically include para-methylethylbenzene (p-MEB) and 1,2,4-trimethylbenzene (1,2,4-TMB). In some embodiments, the heavy reformate stream may contain at least 15 weight percent (wt. %) MEB and at least 50 wt. % TMB. In some embodiments, the heavy reformate stream may contain at least 30 wt. % MEB and at least 70 wt. % TMB. The heavy reformate stream may have from 15 to 30 wt. % MEB, from 20 to 25 wt. % MEB, from 15 to 25 wt. % MEB, or greater than or equal to 30 wt. % MEB. Additionally, the heavy reformate stream may contain from 50 to 70 wt. % TMB, 55 to 65 wt. % TMB, 55 to 70 wt. % TMB, or greater than 70 wt. % TMB.

These aromatics present in the HR fraction (MEB and TMB) can be converted into more valuable BTX compounds by dealkylation of the $C_{9+}$ alkylaromatics, by transalkylation with benzene or toluene, or both. The aim is to maximize the production of xylenes by de-ethylation of MEB and transalkylation of TMB. Specifically, TMB is usually transalkylated using toluene that is formed as a product by the de-ethylation of MEB (which produces toluene and ethylene) to produce more xylenes.

The dealkylation of MEB to toluene and ethane is provided in Scheme 1, infra. Dealkylation of MEB in the presence of a Brønsted acid catalyst initially produces toluene and ethylene. The term "Brønsted acid catalyst" refers to a compound which is able to donate a proton to another molecule, which will be then protonated. However, the ethylene may be subsequently hydrogenated to ethane in the presence of an adequate hydrogenation catalyst. If the hydrogenation functionality is not effective, portions of the ethylene may not be hydrogenated to ethane and as such may be present in the product gases, or it may be converted to oligomers or other products.

Scheme 1

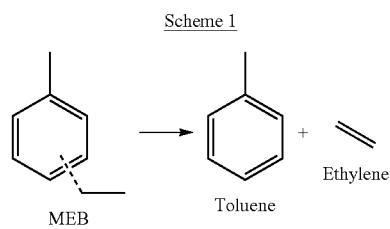

MEB    Toluene    Ethylene

The transalkylation of TMB present in the heavy reformate with the toluene formed from dealkylation of MEB to toluene and ethylene is provided in Scheme 2.

Scheme 2

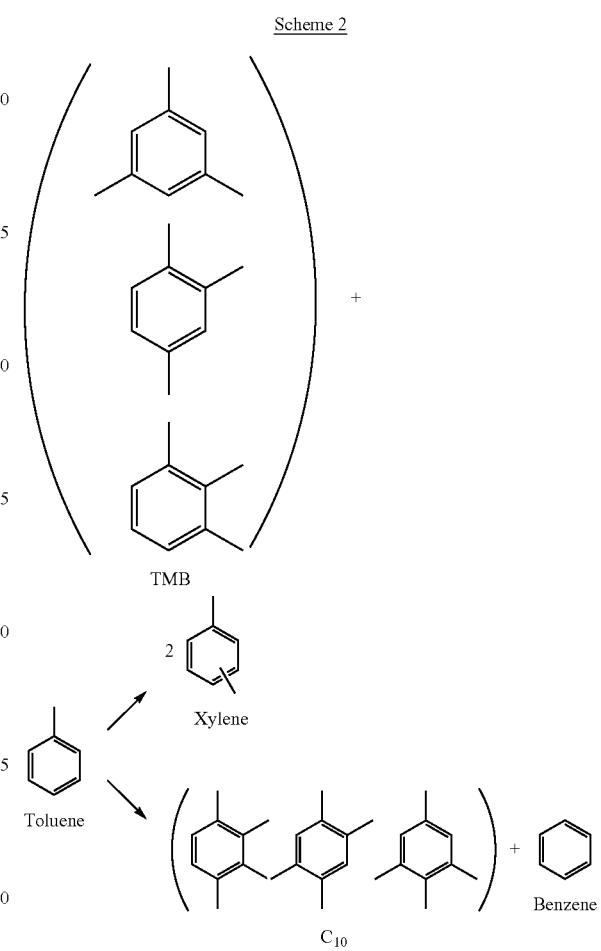

Additionally, toluene and TMB can also undergo disproportionation reactions leading to xylenes and benzene or xylenes and tetramethylbenzenes, respectively. The chemical reactions are provided in Scheme 3.

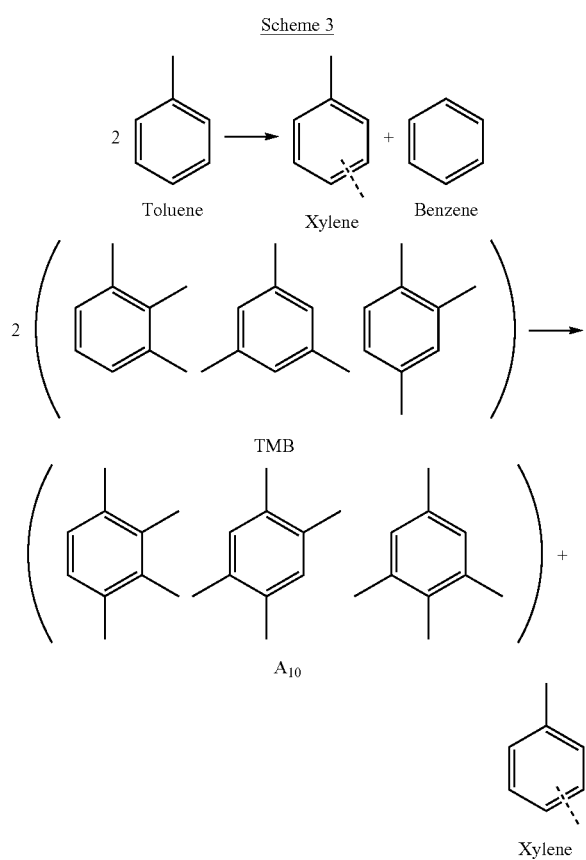

Scheme 3

The heavy reformate stream may be fed into a reactor together with hydrogen ($H_2$). In some embodiments, the heavy reformate stream may be fed into a reactor with hydrogen in a hydrogen/hydrocarbon molar ratio of 8.5. In other embodiments, the molar ratio may be from 8 to 9, or from 7 to 10, or from 7.5 to 9.5. The heavy reformate feed may be fed to the reactor together with hydrogen in from a 10:1 to a 1:1 mol/mol ratio of hydrogen to hydrocarbon. In some embodiments, the heavy reformate feed may be fed to the reactor together with hydrogen in a 4:1 mol/mol ratio of hydrogen to hydrocarbon, or a 5:1 mol/mol ratio, or a 3:1 mol/mol ratio.

The reactor may be any suitable vessel. Possible reactors include, but are not limited to one or more fixed bed reactors, batch reactors, or riser reactors. The reactor may be operated at a temperature between 300° C. and 500° C., such as between 350° C. to 450° C., or 350° C. to 400° C. For instance, the reactor may be operated at a temperature of 350° C., 375° C., or 400° C. The upgrading reactions in the reactor may occur at a pressure of 20 bar. The reactor contains a composite zeolite catalyst containing desilicated mesoporous mordenite and ZSM-5 that is able to catalyze the transalkylation and dealkylation reactions simultaneously.

As mentioned, the composite zeolite catalyst used in the methods of the present embodiments contains a desilicated mesoporous mordenite and ZSM-5. Without being bound by any particular theory, the desilicated mesoporous mordenite and ZSM-5 may work in conjunction to produce a synergistic effect, making the composite zeolite catalyst capable of converting the heavy reformate feed to BTX compounds in a single reactor. Moreover, the composite zeolite catalyst is able to simultaneously catalyze both the dealkylation and transalkylation reactions within the same reactor at the same time. This surprising technical effect of synergistically utilizing both desilicated mesoporous mordenite and ZSM-5 may produce more BTX compounds, in a faster, more efficient system that occurs simultaneously in one reactor, saving time and resources over conventional methodology.

Mordenite is a zeolite mineral with the chemical formula $XAl_2Si_{10}O_{24} \cdot 7H_2O$, in which X can be Ca, $Na_2$, or $K_2$. The molecular framework of mordenite contains chains of five-membered rings of linked silicate and aluminate tetrahedra, and its crystalline structure presents mono-directional channels defined by twelve-membered rings. Mordenite zeolite can also be synthesized starting from its components' precursors, with a broader silica to alumina molar ratio in the range of 6 to 30, and is mainly used as a catalyst in the petrochemical industry, due to its unidirectional channel system. An alkaline solution may desilicate the mordenite, producing a lesser silica (Si) to aluminum (Al) ratio and a more mesoporous zeolite.

Embodiments for making a desilicated mesoporous mordenite include heating a mordenite compound in an inert atmosphere to produce an acid mordenite. As used in this disclosure, "mordenite compound" refers to a raw, commercially available, synthesized by procedures well known by those skilled in the art or occurring in nature mordenite material prior to desilication and dealumination, as described in this disclosure. The acid mordenite may be dealuminated with a first acid treatment to form a dealuminated mordenite. The term "dealuminated" does not exclude the presence of aluminum in the mordenite, but merely indicates that there is a reduction in the amount of aluminum in the dealuminated mordenite when compared to the acid mordenite and the mordenite compound.

Subsequently, the dealuminated mordenite may be desilicated with a basic solution to form a desilicated mordenite. The term "desilicated" does not exclude the presence of silica in the desilicated mordenite, but merely describes that there is a reduction in the amount of silica in the desilicated mordenite when compared to the dealuminated mordenite, the acid mordenite, and the mordenite compound. For purposes of this disclosure, the terms "desilicated mordenite" and "dealuminated mordenite" do not limit or define the pore structure of the mordenite, and mesopores may be present on the dealuminated mordenite and the desilicated mordenite.

Other embodiments for making a desilicated mesoporous mordenite include heating a mordenite compound in an inert atmosphere to produce an acid mordenite. Subsequently, the acid mordenite may be desilicated as described supra without being previously dealuminated. Preparation with direct desilication of the acid mordenite provides a simpler protocol, and higher solid yields.

The desilicated mordenite may be further treated with a second treatment to produce desilicated mesoporous mordenite in its acid form. This desilicated acid mesoporous mordenite may have a Si to Al molar ratio of at least 5, as measured by Inductive Coupling Plasma Mass Spectrometry (ICP-MS), and may have a micropore to mesopore volume ratio of less than 3.0. In further embodiments, desilicated acid mesoporous mordenite may have a Si to Al molar ratio of at least 30 and may have a micropore to mesopore volume ratio of less than 2.0

The desilicated mesoporous mordenite, a zeolite component modified by dealumination and desilication or solely desilication as described in this disclosure, is produced from a commercial mordenite in ammonic form (MOR). MOR may be converted into an acid mordenite (MOR-A) by a mild treatment of heat in an inert atmosphere thus forming MOR-A. The inert atmosphere may include nitrogen gas ($N_2$) or a noble gas such as argon (Ar) or helium (He). The mild treatment includes heating to temperature from 350° C. to 410° C., increasing the heat from room temperature to approximately 400° C. at a rate of 3° C. per minute.

The MOR-A may be dealuminated with a first acid treatment. In one or more embodiments, the first acid treatment includes heating or refluxing the acid mordenite in one or more acid solutions, in which the acid solutions may be different acids with a range of molarities. The acid solutions may include, but are not limited to: strong acids such as nitric acid, hydrochloric acid, sulfuric acid, perchloric acid, hydrobromic acid, and chloric acid; and weak acids such as phosphoric acid, acetic acid, oxalic acid, trichloroacetic acid, ammonium; and a combination of acids. When the first acid treatment comprises more than one acid solution, the acid solutions may be added sequentially. The molarities of the first acid solution may range from 0.1 molar (M) to 5.0M or from 1.0M to 4.0M depending on the acid chosen. In some embodiments, the first acid treatment may include (A) refluxing the acid mordenite in a nitric acid solution, (B) refluxing the acid mordenite in a hydrochloric solution one or more times, or both (A) and (B).

The acid mordenite (MOR-A) or the dealuminated mordenite is desilicated in a basic solution to form the desilicated mordenite. As briefly mentioned in the previous paragraphs, the desilicated mesoporous mordenite is synthesized by at least a desilication step, or by combination of a dealumination and a desilication step. As used in this description, desilicated mesoporous mordenite implies a mordenite compound that has undergone at least one desilication step. In one embodiment, the basic solution may comprise an alkali or alkaline metal hydroxide and can include, but is not limited to: sodium hydroxide, lithium hydroxide, calcium hydroxide, potassium hydroxide, ammonium hydroxide, magnesium hydroxide, beryllium hydroxide, barium hydroxide, and cesium hydroxide. The molar content of the basic solution can range from 0.05M to 2.0M, 0.1M to 1.0M, or 0.2 to 0.75M. Acid or dealuminated mordenite is treated in the basic solution for between 15 minutes to 2 hours, between 20 minutes and one hour, or approximately 30 minutes, at a temperature between 40° C. and 95° C., between 50 and 90° C., or between 65 and 85° C. Treatment temperature is an important parameter of the desilication treatment.

In further embodiments, the desilicated mordenite is further treated with a second treatment to obtain the desilicated mesoporous mordenite in its acid form. The second treatment may comprise an acid solution or an ammonic solution. The acid solution may be chosen from nitric acid, hydrochloric acid, phosphoric acid, sulfuric acid, perchloric acid, hydrobromic acid, chloric acid, acetic acid, trichloroacetic acid, oxalic acid, or combinations thereof. The ammonic solution may be chosen from ammonium nitrate, ammonium chloride, or combinations thereof. The molarities of the second acid solution may range from 0.1M to 2.0M or from 0.1M to 1.0M, depending on the acid chosen. The first acid treatment and the second treatment may involve the addition of one or multiple sequential acid solutions.

In one or more embodiments, the desilicated mesoporous mordenite may have a micropore volume ($V_{micro}$) of at least 0.10 cubic centimeters per gram ($cm^3/g$), or a micropore volume of at least 0.15 $cm^3/g$, or a micropore volume of between 0.15 to 0.20 $cm^3/g$. The micropore volume may be calculated by the t-plot method of determining micropore volume known to one having skill in the art. In one or more embodiments, the desilicated mesoporous mordenite may have a mesopore volume ($V_{meso}$) of at least 0.08 $cm^3/g$. In other embodiments, the desilicated mesoporous mordenite may have a micropore volume of between 0.10 to 0.30 $cm^3/g$, between 0.14 to 0.28 $cm^3/g$, or between 0.16 to 0.25 $cm^3/g$. The mesopore volume may be calculated according to the Barrett-Joiner-Halenda (BJH) method of determining mesopore volume known to one having skill in the art. Details regarding the t-plot method and the BJH method of calculating micropore volume and mesopore volume respectively are provided in Galarneau et al., "Validity of the t-plot Method to Assess Microporosity in Hierarchical Micro/Mesoporous Materials", Langmuir 2014, 30, 13266-13274, for example. In one or more embodiments, the desilicated acid mesoporous mordenite may have a Si to Al molar ratio of at least 5, as measured by ICP-MS, and may have a micropore to mesopore volume ratio of less than 3.0.

In some embodiments, the desilicated mesoporous mordenite may have a surface area defined by a Brunauer-Emmett-Teller (BET) analysis ($S_{BET}$) of at least 460 square meters per gram ($m^2/g$), a $S_{BET}$ surface area of at least 500 $m^2/g$, or the $S_{BET}$ surface area can be between 500 $m^2/g$ and 580 $m^2/g$. Further, the desilicated mesoporous mordenite may have a micropore surface area ($S_{micro}$) of 300 $m^2/g$ to 420 $m^2/g$ or of 330 $m^2/g$ to 390 $m^2/g$. The micropore surface area may be calculated directly from the micropore volume.

In one or more embodiments, the desilicated mesoporous mordenite may have an external surface area ($S_{Ext}$) of at least 80 $m^2/g$. In various other embodiments, the desilicated mesoporous mordenite may have an external surface area of between 90 to 360 $m^2/g$, between 95 to 250 $m^2/g$, between 150 to 360 $m^2/g$, or between 160 to 250 $m^2/g$. It is noted that the external surface area is obtained as the difference between the BET surface area and the micropore surface area. In some embodiments, the desilicated mesoporous mordenite has a micropore to mesopore ratio of less than 3.0. In other embodiments the ratio of micropore to mesopore is less than 2.5, less than 2.0, or less than 1.5. In further embodiments the ratio of micropore to mesopore is a range of from 0.3 to 2.0, from 0.3 to 1.2, from 0.5 to 1.2, or from 0.5 to 0.9.

ZSM-5 (Zeolite Socony Mobil-5) is a medium pore zeolite that has a MFI framework with an ordered crystal structure. ZSM-5 is an aluminosilicate zeolite of the pentasil family of zeolites with the chemical formula $Na_nAl_nSi_{96-n}O_{192} \cdot 16H_2O$, and channels defined by ten-membered rings. In one or more embodiments, the ZSM-5 zeolite catalyst is a commercially available ZSM-5. For example, the ZSM-5 may be CBV3024E from Zeolyst International (Conshohocken, Pa., USA). In some embodiments, the ZSM-5 may have a Si to Al molar ratio of at least 10, as measured by ICP-MS. For instance, the ZSM-5 may have a Si to Al molar ratio of at least 15, at least 30, at least 35, or at least 45, as measured by ICP-MS.

In one or more embodiments, the zeolite catalyst may include desilicated mesoporous mordenite (as described in this disclosure) and a metal component, or desilicated mesoporous mordenite mixed with both ZSM-5 and a metal component. In some embodiments, the zeolite catalyst includes the desilicated mesoporous mordenite physically mixed with ZSM-5, having a weight ratio of ZSM-5 to desilicated mesoporous mordenite from greater than 0 to 1.0. In some embodiments, the zeolite catalyst includes the desilicated mesoporous mordenite impregnated with a metal component selected from the group consisting of Group VI and Group VII metals according to IUPAC nomenclature, in which the metal component is an amount from 0.05 weight percent (wt. %) to 10 wt. %, based on the total weight of the zeolite catalyst. In one or more embodiments, the zeolite catalyst includes desilicated mesoporous mordenite impregnated with a metal component and physically mixed with ZSM-5. In some embodiments, the zeolite catalyst includes desilicated mesoporous mordenite impregnated with a metal component and physically mixed with ZSM-5 impregnated with the metal component. In the zeolite catalyst, the desilicated mesoporous mordenite has a Si to Al molar ratio of at least 5 as measured by ICP-MS, and a micropore to mesopore volumetric ratio of less than 3.0. In further embodiments, in the zeolite catalyst, the desilicated mesoporous mordenite has a Si to Al molar ratio of at least 30 as measured by ICP-MS, and a micropore to mesopore volumetric ratio of less than 2.0.

In one or more embodiments, the desilicated mesoporous mordenite and the ZSM-5 zeolite are combined in a 50:50 to 90:10 weight ratio to form the composite zeolite catalyst. In various further embodiments, the desilicated mesoporous mordenite and ZSM-5 are combined in a 50:50 to 80:20 weight ratio. Without being bound by theory, the weight ratio of desilicated mesoporous mordenite and ZSM-5 determines the relative dealkylation-transalkylation capacity of the zeolite catalyst. ZSM-5 is believed to be primarily responsible for MEB dealkylation and mordenite is believed to be primarily responsible for catalyzing the transalkylation reaction of the TMB. In some particular embodiments, the catalyst may contain a combination of desilicated mesoporous mordenite to ZSM-5 in a weight ratio of 60:40 (1.5) or 80:20 (4.0). In some embodiments, improved catalyst performance may depend on the proportion of mordenite (large pore transalkylation component), which is desirably present in greater amounts than that of ZSM-5 (medium pore dealkylation component).

In some embodiments, the metal component may be loaded or impregnated onto a zeolite component: either ZSM-5, desilicated mesoporous mordenite, or both. When the metal component is loaded onto the zeolite component, the resulting zeolite catalyst may be referred to as the "metal loaded zeolite catalyst," "zeolite catalyst," or as otherwise defined. Moreover, the zeolite catalysts may be impregnated with a metal chosen from a Group VI and Group VII metal according to IUPAC nomenclature. For example, the metal may be chosen from molybdenum, chromium, nickel, tungsten, palladium, ruthenium, gold, rhenium, rhodium, or combinations thereof. In some embodiments of the zeolite catalyst, the metal component is rhenium (Re). The rhenium content can be measured by ICP-MS. There are various options for depositing or loading the metal component onto the zeolite catalyst. In one or more embodiments, the metal is loaded onto the zeolite catalyst via incipient wetness procedure. Other methods of adding the metal component to the zeolite catalyst include ion exchange or wet impregnation, in which the zeolite is contacted with an excess of the metal salt solution.

The metal component may exist within the final zeolite catalyst as a compound, such as an active metal oxide, an active metal sulfide or active metal halide, in chemical combination with one or more of the other ingredients of the composite, or as an elemental metal. The metal component may be present in the metal loaded zeolite catalyst in any amount that is catalytically effective, for example from 0.01 to 20.0 wt. %, or from 0.05 wt. % to 10 wt. %, or from 0.1 to 6.0 wt. %, or approximately from 0.25 to 0.55 wt. %, based on the total weight of the zeolite catalyst.

In further embodiments, the desilicated mesoporous mordenite when combined with ZSM-5 and rhenium (Re) achieves improved performance in dealkylation and transalkylation conversion of heavy reformate as compared to monozeolite-based catalysts or as compared to multi-zeolite based catalysts prepared by physical mixtures of unmodified individual zeolite components (See. FIGS. 8A-9C). The term "unmodified" as used in this disclosure means that the zeolite has not been modified and that the zeolite is commercially available or naturally occurring. The term "modified" means a component, specifically a zeolite, chemically treated to alter the chemical or physical composition or the textural properties.

Figure 1B:
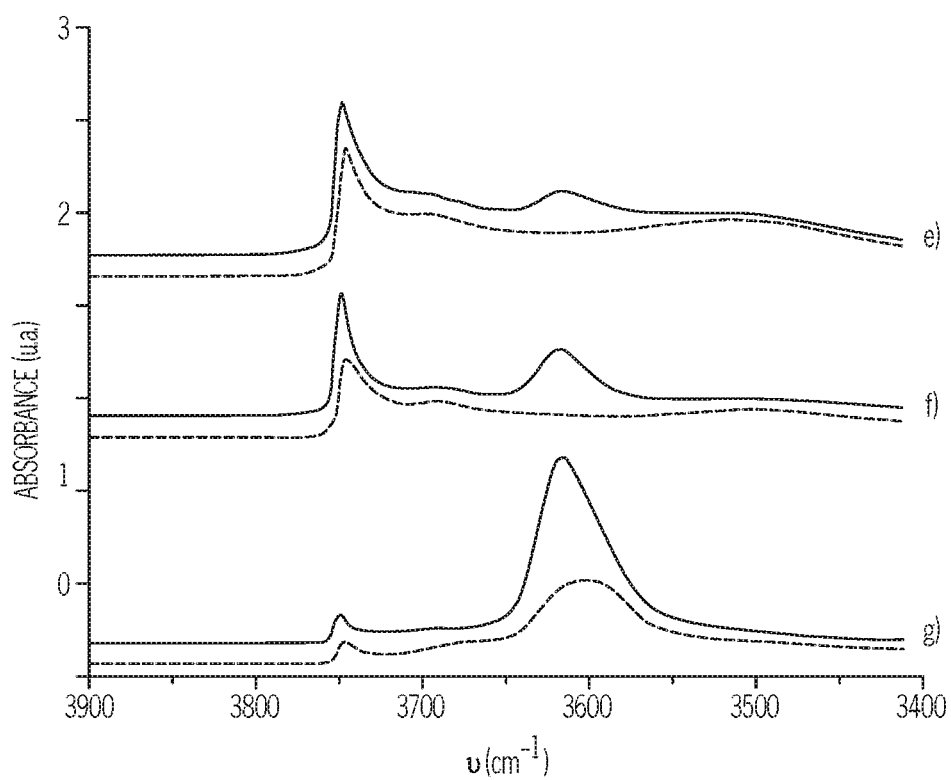
FIG. 1B is a FT-IR spectra of a hydroxyl region of mordenite samples. The solid lines correspond to the spectra recorded after each mordenite sample was pretreated at 400° C. under vacuum, and the dotted lines correspond to the spectra recorded after pyridine adsorption and desorption at 150° C. The mordenite samples are described in the Example section infra and are as follows: e) Cat. 4, f) Cat. 3, and g) MOR.
Figure 1C:
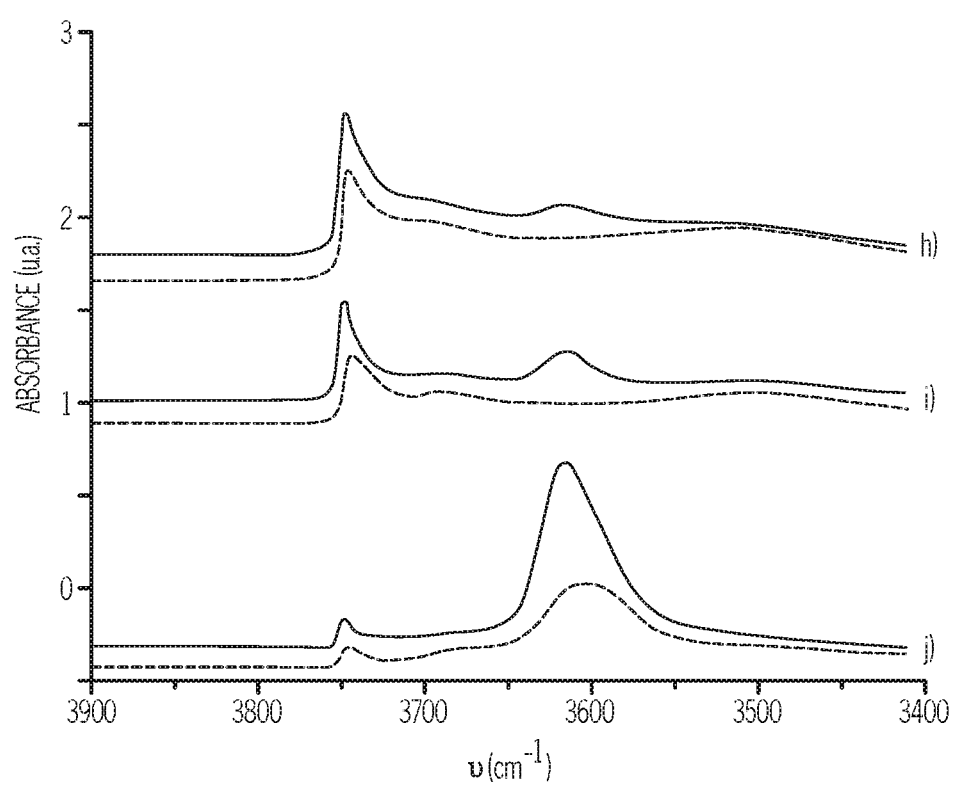
FIG. 1C is a FT-IR spectra of a hydroxyl region of mordenite samples. The solid lines correspond to the spectra recorded after each mordenite sample was pretreated at 400° C. under vacuum, and the dotted lines correspond to the spectra recorded after pyridine adsorption and desorption at 150° C. The mordenite samples are described in the Example section infra and are as follows: h) Cat. 6, i) Cat. 5, and j) MOR.

When mordenite is desilicated, the surface area of the zeolite changes. The surface area has more mesopores compared to the unmodified mordenite, MOR (See infra. Table 2). The increase in the volume of mesopores increases the number of accessible active sites (See infra. FIGS. 1A-1C).

As mentioned, the composite zeolite catalyst may be impregnated with rhenium (Re). In some particular embodiments, the desilicated mesoporous mordenite impregnated with rhenium may have a surface area defined by a Brunauer-Emmett-Teller (BET) analysis ($S_{BET}$) of at least 450 square meters per gram ($m^2/g$), a $S_{BET}$ surface area of at least 500 $m^2/g$, or the $S_{BET}$ surface area can be between of 500 $m^2/g$ and 550 $m^2/g$. Further, the desilicated mesoporous mordenite impregnated with rhenium may have a micropore surface area ($S_{micro}$) of 280 $m^2/g$ to 400 $m^2/g$ or of 315 $m^2/g$ to 370 $m^2/g$. The micropore surface area may be calculated directly from the micropore volume.

In one or more particular embodiments, the desilicated mesoporous mordenite impregnated with rhenium may have an external surface area ($S_{Ext}$) of at least 80 $m^2/g$; in other embodiments, it may have an external surface area of between 90 to 350 $m^2/g$ or between 95 to 240 $m^2/g$. It is noted that the external surface area is obtained as the difference between the BET surface area and the micropore surface area.

In one or more particular embodiments, the desilicated mesoporous mordenite impregnated with rhenium may have a micropore volume ($V_{micro}$) of at least 0.10 cubic centimeters per gram ($cm^3/g$), or a micropore volume of at least 0.14 $cm^3/g$, or a micropore volume of between 0.15 to 0.19 $cm^3/g$. In some embodiments, the desilicated mesoporous mordenite impregnated with rhenium may have a mesopore volume ($V_{meso}$) of at least 0.08 cubic centimeters per gram ($cm^3/g$), or a mesopore volume of at least 0.11 $cm^3/g$. In other embodiments, the desilicated mesoporous mordenite impregnated with rhenium may have a mesopore volume of between 0.14 to 0.28 $cm^3/g$ or between 0.16 to 0.25 $cm^3/g$.

The micropore volume and the mesopore volume represent the specific volumes corresponding to the microporous structure and to the mesoporous structure, respectively. The mesopores are mainly due to intracrystalline voids generated by means of the desilication treatment. The pore size ranges for mesopores and micropores are in conformity with conventionally understood size ranges for such pore classifications with micropores representing pores under 2 nanometers (nm) in diameter and mesopores representing pores of 2 to 50 nm in diameter. A total pore volume would additionally include any macropores, if present.

In one or more embodiments, the composite zeolite catalyst includes desilicated mesoporous mordenite. The desilicated mesoporous mordenite, the product of the dealumination treatment and/or the desilication treatment, has a micropore to mesopore ratio of less than 3.0 and a molar ratio of silica to aluminum of greater than 5 as measured by ICP-MS.

In one or more embodiments, the desilicated mesoporous mordenite, has a micropore to mesopore ratio of less than 3.0; in other embodiments, the ratio of micropore to mesopore is less than 2.5, or in further embodiments the ratio of micropore to mesopore is a range of from 0.3 to 2.0 or from 0.5 to 1.2.

In other embodiments, the desilicated mesoporous mordenite has molar ratios of Si to Al of greater than 5; in other embodiments the silica to aluminum ratio is greater than 6; in further embodiments the silica to aluminum ratio is from between 10 and 60 as measured by ICP-MS. In one or more embodiments, the silica to aluminum molar ratio is from between 30 and 50 as measured by ICP-MS.

In some embodiments, the composite zeolite catalyst includes desilicated mesoporous mordenite mixed with ZSM-5, a metal component, or both, in accordance with any of the embodiments previously described. When the zeolite catalyst includes desilicated mesoporous mordenite and ZSM-5, there is a weight ratio of ZSM-5 to desilicated mesoporous mordenite from greater than 0 to 1.0. Then, a hydrogen gas and hydrocarbon feed stream output may be adjusted to a molar ratio of between 2 and 10 or between 3 and 8. In some embodiments, the hydrogen gas and hydrocarbon feed stream output is a ratio of 4. This reaction occurs for a reaction time and at a reaction temperature. The reaction temperature includes a constant temperature of from between 300° C. to 500° C., from between 350° C. to 450° C., or from between 350° C. to 400° C. or at a constant temperature of 350° C., 375° C. or 400° C. The reaction time includes times of less than an hour to 120 hours, from 15 minutes to 100 hours, and 1 hour to 60 hours.

Without being bound by any particular theory, the composite zeolite catalyst allows conversion of heavy reformate, or other aromatic reactant streams, in a single reactor. Specifically, the $C_{9+}$ dealkylation of MEB and the transalkylation of the produced toluene with TMB may be performed in a single reactor. The MEB dealkylation reaction is necessary in order to obtain the toluene that has to react with the TMB in the feed for producing the desired xylenes. Thus, the composite zeolite catalyst obtained by the one pot synthesis of the zeolite catalyst enables an improved and faster coupling of both consecutive reactions as compared with conventional multi-zeolite catalysts.

Embodiments of this disclosure include a "one-pot" method of transalkylating and dealkylating heavy reformate, referring to both reactions occurring in the same reactor. In conventional systems, alkylaromatics, such as those present in a heavy reformate fraction (MEB, TMB), in the presence of a Brønsted acid catalyst as described supra, may undergo undesired reactions which lead to the formation of aromatics with more than 10 carbon atoms ($A_{10+}$). If these $A_{10+}$ compounds cannot diffuse out of the composite zeolite crystals through the pores of the crystalline structure because of steric limitations, they may block part of the channel systems or lead to bulkier coke precursors.

Without being bound by any particular theory, the "one-pot" nature of the present method, in which both dealkylation and transalkylation occur in one reactor, may lead to the improved conversion efficiency of the composite zeolite catalysts by alleviating the formation of heavy alkylaromatics. Specifically, the mesopores in the composite zeolite catalyst allow for easier diffusion of the reactants present in the feed stream (MEB and TMB), as well as the toluene produced from de-ethylation of MEB. This enhanced diffusion of reactants and products helps to prevent them from being involved in non-desired secondary reactions, such as disproportionation and/or transalkylation. Specifically, the proximity of the desilicated mesoporous mordenite and ZSM-5 within a single reactor allows the TMB to react preferentially with the toluene produced from the dealkylation of MEB instead of reacting with other TMB compounds to form tetramethylbenzene or other heavier compounds. The specific properties of the composite zeolite catalyst, such as a small ratio of micropores to mesopores and more accessible Brønsted acid sites, results in greater selectivity to xylene and reduced formation of $A_{10+}$ and coke precursors, leading therefore to improved catalyst life and greater product yields.

Additionally, the reaction of the heavy reformate feed in a single reactor with the composite zeolite catalyst comprising desilicated mesoporous mordenite and ZSM-5 achieves improved performance in conversion of the heavy reformate to BTX compounds. This improvement is even more profound when carrying out the transalkylation of a heavy reformate in the absence of added toluene or benzene, because these two aromatics must be produced in-situ from $C_{9+}$ aromatics such as with dealkylation of MEB contained within the feed. Again, without intent to be bound by any particular theory, it is believed that the proximate locations of the desilicated mesoporous mordenite and ZSM-5 in the composite zeolite catalyst through a physical mixture and reaction in a single reactor allows the toluene produced from dealkylation of MEB to be more readily available for use in the transalkylation reaction of TMB or disproportionation reaction of toluene for the ultimate production of xylenes.

As such, in some embodiments, the method of the present embodiments may produce a yield of at least 80 wt. % BTX compounds, as measured based on the total weight of the heavy reformate stream. The method may produce a yield of at least 85 wt. %, at least 90 wt. %, or at least 95 wt. % BTX compounds, as measured based on the total weight of the heavy reformate stream. Additionally, the method may not require extreme temperatures to achieve these increased yields. In some embodiments, the method of the present embodiments may produce a yield of at least 80 wt. % BTX compounds at less than or equal to 400° C., such as 400° C., 375° C., 350° C., or 300° C. The method may produce a yield of at least 85 wt. %, at least 90 wt. %, or at least 95 wt. % BTX compounds, at temperatures of less than or equal to 400° C., less than or equal to 375° C., less than or equal to 350° C., or less than or equal to 300° C.

As mentioned, the method of the present embodiments may provide an increased yield of xylene. In some embodiments, the method may produce a yield of at least 15 wt. % xylene, as measured based on the total weight of the heavy reformate stream. The method may produce a yield of at least 20 wt. %, at least 25 wt. %, at least 30 wt. %, or at least 50 wt. % xylene, as measured based on the total weight of the heavy reformate stream. Similarly, the method of the present embodiments may decrease the production of unwanted aromatic compounds, such as those having 10 or more carbon atoms ($C_{10+}$). In some embodiments, the method may produce less than or equal to 20 wt. % of aromatic compounds having 10 or more carbon atoms, as measured based on the total weight of the heavy reformate stream. For instance, the method may produce less than or equal to 15 wt. %, less than or equal to 10 wt. %, or even less than or equal to 5 wt. % of aromatic compounds having 10 or more carbon atoms, as measured based on the total weight of the heavy reformate stream.

Examples

Synthesis of Desilicated Mordenite and Zeolite Catalyst

Commercially supplied mordenite was used throughout the experiments. An example of commercially available mordenite is CBV21A ("MOR"), sold by Zeolyst International of Conshohocken, Pa., U.S.A.

The commercial mordenite (CBV21A) was supplied in its ammonic form, which means that the negative charge generated by the isomorphic substitution of the $Si^{4+}$ by $Al^{3+}$ in tetrahedral coordination is compensated by $NH_4^+$ cations, instead of H. Therefore, the commercially supplied mordenite needed to be calcined for decomposition of the ammonium ions into $NH_3$ and a proton bonded to the zeolite framework. The protons ($H^+$) confer to the zeolite its Brønsted acidity. To insure that the zeolite was in its acidic form, MOR-A, the zeolite was heated at 400° C. for three hours under flowing nitrogen gas (150 ml/min). This mild treatment prevented framework dealumination. Afterwards, three independent acid treatment procedures were used independently to reduce the aluminum content in the mordenite component.

Dealumination: The First Acid Treatment

In acid treatment 1, MOR-A zeolite was refluxed at 70° C. for 4 hours under rigorous stirring in 1.0M nitric acid aqueous solution. Then, the solid was filtered, washed with distilled water until the pH of the water was 7. The obtained solid was dried overnight at 100° C.

In acid treatment 2, the MOR-A zeolite was dealuminated by means of two separate and consecutive hydrochloric acid (HCl) washes of 4.0M at 80° C. for 30 minutes, refluxed under vigorous stirring, then calcined in an oven at 500° C. for 4 hours. A final dealumination step occurred when the calcined zeolite was refluxed for four hours in a 1.0M nitric acid solution at 70° C. under vigorous stirring. After each acid wash, the solid was filtered, washed with distilled water until the water had a pH of 7 and there was an absence of chlorides in the washing water. Then, the solid was dried at 100° C. overnight.

In acid treatment 3, MOR-A zeolite was washed three consecutive times with a 4.0M hydrochloric acid solution at 80° C. for 30 min, refluxed under vigorous stirring. The sample was calcined in muffle at 500° C. for 4 hours after the last HCl wash. The final dealumination step occurred when the recovered solid was refluxed in a 1.0M nitric acid solution at 70° C. for 4 hours under vigorous stirring. After each acid wash the solid was filtered, washed with distilled water until the wash water had a pH of 7 and did not contain chlorides. The dealuminated mordenite was dried at 100° C. overnight.

Desilication Step

After the mordenite was subjected to one of the three acid treatments, the resulting dealuminated mordenite underwent a desilication step. The desilication step was performed by contacting the dealuminated mordenite with a 0.2M sodium hydroxide (NaOH) solution, at 85° C. under vigorous stirring for 30 min, followed by washing with distilled water until the water had a pH of 7, and drying at 100° C. overnight.

Sodium Ion Removal: the Second Treatment

To obtain the final acid form of the desilicated mesoporous mordenite, excess sodium ions ($Na^+$) were removed. According to the chemical composition obtained by ICP-MS, the $Na^+$ content in the final desilicated mesoporous mordenite after this $Na^+$ removal step was low, with Na/Al of 0.1 or less.

In one procedure, the dealuminated mordenite was refluxed in a 0.1M solution of ammonium nitrate ($NH_4NO_3$) or ammonium chloride ($NH_4Cl$) at 80° C. for 2 hours, while vigorously stirring. The solution was washed with 3 liters of distilled water per gram of zeolite, and dried at 100° C. overnight.

An alternate procedure, the oxalic acid treatment, removed the $Na^+$ when the dealuminated mordenite was refluxed in a 0.8M solution of oxalic acid ($H_2C_2O_4$) at 80° C. for 2 hours, while under vigorous stirring. The solution was washed with distilled water until water had a pH of 7, dried at 100° C. overnight, and calcined at 375° C. for 3 hours. Since after this treatment the $Na^+$ was not exchanged completely, a second exchanged was required, in this case with a 2.5 M $NH_4Cl$ solution, which was refluxed at 80° C. for 2 hours, under vigorous stirring; the resulting product was washed with distilled water until absence of $Cl^-$, and drying at 100° C. overnight. The oxalic acid treatment employed can be further optimized by decreasing acid concentration, temperature and time of the treatment, in order to limit dealumination to the external surface of the crystallites, and to avoid framework dealumination.

Metal Impregnation Step

After the mordenite was desilicated and the excess $Na^+$ was removed, the resulting desilicated mesoporous mordenite was impregnated with rhenium via an incipient wetness procedure using ammonium perrhenate ($NH_4ReO_4$) as a metal precursor. After the metal loading the samples were stored in a desiccator for at least 5 hours, and then dried at 100° C. overnight. Unless otherwise specified, the samples were calcined in a fixed bed reactor. Temperature was increased up to 500° C. in 100 mL/min of $N_2$ at a heating rate of 3° C. per min, maintained at 500° C. for 3 hours under air flow (100 mL/min), and then cooled to room temperature or to the activation temperature under $N_2$ flow (100 mL/min). Room temperature is defined as 22±2° C.

As follows, seven different samples were compared to the calcined commercial starting material, MOR-A, and another commercial catalyst, ATA-21. Each sample was prepared by a combination of the previously described methods. The catalyst preparation methods are listed in the following paragraphs. The desilicated mesoporous mordenite and the respective physicochemical properties are presented in Table 2, infra.

Catalyst 1

To prepare Catalyst 1, MOR was converted to MOR-A. MOR-A was treated with acid treatment 1, then desilicated, and then treated with ammonium for the ion exchange or $Na^+$ removal. When Catalyst 1 was loaded with rhenium, Rhenium Catalyst 1 (Re Cat. 1) was formed.

Catalyst 2

To prepare Catalyst 2, MOR was converted to MOR-A. MOR-A was treated with acid treatment 1, then desilicated, and then treated with oxalic acid for the ion exchange or $Na^+$ removal. When Catalyst 2 was loaded with rhenium, Rhenium Catalyst 2 (Re Cat. 2) was formed.

Catalyst 3

To prepare Catalyst 3, MOR was converted to MOR-A. MOR-A was treated with acid treatment 2, then desilicated, and then treated with ammonium for the ion exchange or $Na^+$ removal. When Catalyst 3 was loaded with rhenium, Rhenium Catalyst 3 (Re Cat. 3) was formed.

Catalyst 4

To prepare Catalyst 4, MOR was converted to MOR-A. MOR-A was treated with acid treatment 2, then desilicated, and then treated with oxalic acid for the ion exchange or $Na^+$ removal. When Catalyst 4 was loaded with rhenium, Rhenium Catalyst 4 (Re Cat. 4) was formed.

Catalyst 5

To prepare Catalyst 5, MOR was converted to MOR-A. MOR-A was treated with acid treatment 3, then desilicated, and then treated with ammonium for the ion exchange or $Na^+$ removal. When Catalyst 5 was loaded with rhenium, Rhenium Catalyst 5 (Re Cat. 5) was formed.

Catalyst 6

To prepare Catalyst 6, MOR was converted to MOR-A. MOR-A was treated with acid treatment 3, then desilicated, and then treated with oxalic acid for the ion exchange or $Na^+$ removal. When Catalyst 6 was loaded with rhenium, Rhenium Catalyst 6 (Re Cat. 6) was formed.

of the basic desilication procedure, for example the sodium hydroxide (NaOH) concentration, treatment time, and temperature, based on the initial aluminum (Al) content of the parent mordenite.

The yield of desilicated mesoporous mordenite, in weight percent (wt. %), obtained at the end of the treatment of the mordenite compounds prepared are included in Table 1, supra. The yield decreased as the degree of dealumination of the parent zeolite increased. Thus, the final yield of the procedure could be controlled based on the initial amount of Al in the starting mordenite, and to obtain final desilicated mesoporous mordenite with different proportions of micro- and mesoporosity. Typically, the Si/Al ratios in non-modified mordenite are in the range of 6 to 30.

As previously mentioned, when comparing the final samples obtained by ammonium ion ($NH_4^+$) exchange (Cats. 1, 3, and 5) to the samples obtained by oxalic acid treatment (Cats. 2, 4 and 6), the oxalic acid treatment resulted in a

TABLE 2

Physicochemical Properties of the Desilicated Mesoporous Mordenite Compounds

| Sample | ICP-MS Si/Al | ICP-MS Na/Al | Si/Al (XPS) | $S_{Bet}$ (m²/g) | $S_{micro}$ (m²/g) | $S_{Ext}$ (m²/g) | $V_{micro}$ (cm³/g) | $V_{meso}$ (cm³/g) | $V_{micro}/V_{meso}$ | Yield (wt. %) |
|---|---|---|---|---|---|---|---|---|---|---|
| MOR | 10 | 0.00 | 18.7 | 451 | 425 | 26 | 0.204 | 0.029 | 7.03 | — |
| Cat. 1 | 13 | 0.04 | 22.1 | 551 | 390 | 161 | 0.193 | 0.161 | 1.20 | 58 |
| Cat. 2 | 31 | 0.00 | 103.9 | 566 | 383 | 183 | 0.191 | 0.183 | 1.04 | 46 |
| Cat. 3 | 17 | 0.11 | 26.1 | 554 | 338 | 215 | 0.163 | 0.232 | 0.703 | 51 |
| Cat. 4 | 34 | 0.00 | 50.2 | 564 | 331 | 233 | 0.159 | 0.247 | 0.644 | 47 |
| Cat. 5 | 20 | 0.09 | 32.1 | 542 | 358 | 184 | 0.174 | 0.224 | 0.777 | 37 |
| Cat. 6 | 36 | 0.00 | 111.1 | 556 | 371 | 186 | 0.180 | 0.228 | 0.790 | 28 |

Based on the physicochemical properties listed in Table 2, the method described previously desilicated the mordenite. According to the results, Cat. 1-6, which were treated with a dealumination procedure and a desilication treatment, had significantly greater mesopore volume than the commercial MOR, especially those obtained by desilication of mordenite dealuminated by acid treatments 2 and 3, which includes Catalysts 3-6. Acid treatment 1 is milder than treatments 2 and 3, and dealuminated the mordenite zeolite in a lower extentextend. Thus, the final aluminum content of the zeolite after treatment 1 is greater (approximately 14) than after treatments 2 and 3 (close to 25). As mentioned before Si/Al ratios of less than 25 may result in less effective desilication and less mesoporosity generation but larger preservation of the micropore volume.

Catalysts 2, 4, and 6, were treated with oxalic acid to obtain the desilicated mesoporous acid mordenite. The second treatment or the oxalic acid treatment, removed the $Na^+$ ions in addition to aluminum, thereby increasing silica/aluminum (Si/Al) ratios of these catalysts. These greater Si/Al ratio were evidence of further dealumination. The mesopore volume of Catalyst 2 and 4 were greater than those of the catalysts that were treated with ammonium, Catalysts 1, 3. Without being bound by theory, it is believed that this is due to the removal of amorphous extra framework species present in the mesopores formed during the desilication treatment, which are washed out of the mesoporous zeolite during the oxalic acid treatment.

The desilication treatment could have dissolved part of the mordenite, thus generating mesopores, but the final solid yield was controlled by adjusting the severity and extension further dealumination, resulting in Si/Al ratios greater than 30 in each catalyst example. However, the dealumination occurs mainly on the external surface. According to X-ray photoelectron spectroscopy (XPS) results, the surface Si/Al ratios are greater than 50. XPS measurements were performed on the final acid mesoporous mordenites, before adding the Re, and the results are enclosed in Table 2. Not to be bound by theory, but the results indicated that the different aluminum distribution has an effect on the catalytic behavior of the different catalysts compared.

The acidic properties of each of the samples were also quantified. The acidity of the desilicated mesoporous mordenite catalysts was determined by means of Fourier Transform Infrared (FT-IR) spectroscopy combined with the adsorption of pyridine and the progressive desorption at increasing temperatures. Self-supported wafers (10 mg cm²) of calcined samples, previously activated at 400° C. and $10^{-2}$ pascal (Pa) overnight in a Pyrex vacuum cell, were allowed to come in contact with $6.5 \times 10^2$ Pa of pyridine vapor at room temperature and desorbed in vacuum at increasing temperatures (150° C., 250° C., and 350° C.). The spectra were recorded at room temperature. All the spectra were scaled according to the sample weight. The Brønsted and Lewis acidities of the samples were compared and arbitrary units assigned. The units assigned were based on the intensity of the bands assigned to the pyridine interacting with the Brønsted and Lewis acid sites of the zeolites (1550 and 1450 $cm^{-1}$, respectively). These acidic properties are listed in Table 3 infra.

TABLE 3

Acidic Properties of Desilicated Mesoporous Mordenite Compound

| Sample | Brønsted Acidity (a.u.) | | | | Lewis Acidity (a.u.) | | |
|---|---|---|---|---|---|---|---|
| | B150 | B250 | B350 | B350/B150 | L150 | L250 | L350 |
| MOR | 618 | 487 | 373 | 0.48 | 51 | — | — |
| Cat. 1 | 404 | 332 | 185 | 0.46 | 277 | 273 | 248 |
| Cat. 2 | 116 | 94 | 47 | 0.41 | 46 | 39 | 40 |
| Cat. 3 | 240 | 188 | 122 | 0.51 | 204 | 156 | 142 |
| Cat. 4 | 127 | 108 | 60 | 0.47 | 35 | 31 | 30 |
| Cat. 5 | 173 | 129 | 79 | 0.46 | 136 | 10 | 94 |
| Cat. 6 | 93 | 84 | 51 | 0.55 | 32 | 29 | 25 |

According to the results in Table 3 the combination of acidic and basic treatments for mesoporosity generation resulted in a considerable decrease of the number of Brønsted acid sites, especially when the final sample was washed with oxalic acid, which was in agreement with the greater Si/Al ratio (lesser Al content) of these samples. The amount of Brønsted acid sites is related to the amount of Al atoms in framework positions. In order for the Brønsted acid sites to be active for transalkylation, the active sites need to be accessible. However, too many acid sites may detrimentally affect the reaction products: too many exposed sites will enhance conversion of xylenes back to the heavy reformate, too few will prevent the reaction products from forming.

The results in Table 3 illustrated that there was a loss of Brønsted acidity. The loss of Brønsted acidity was confirmed by the decrease in the number of acid sites and not to the non-interaction with pyridine due to sterical hindrance by the bands present in the —OH region of the IR spectra. In FIG. 1, the spectra corresponding to the samples after pretreatment in the IR cell at 400° C. under vacuum (solid lines) with those recorded after pyridine adsorption at 150° C. (dotted lines) were compared. The bands at 3745 cm$^{-1}$ are assigned to Si—OH, as opposed to those appearing at a frequency of 3600 cm$^{-1}$ corresponding to the acid hydroxyls. Comparing the bands before pyridine adsorption (the continuous line) and after pyridine adsorption at 150° C. (the dotted line), all the Brønsted acid sites were accessible for the six desilicated mesoporous mordenite catalysts, whereas a considerable fraction (approximately 40%) of the total Brønsted sites present in the parent microporous mordenite (MOR) were not able to interact with the basic probe molecule, pyridine. Although mordenite is usually considered as a monodimensional large pore zeolite, the structure also presents 8-ring channels, and in the case of the purely microporous zeolite, only the exposed hydroxyls in the 12-ring channels would have interacted with pyridine, as opposed to the exposed hydroxyls in the 8-ring channels, which would have been sterically hindered. The generation of mesoporosity by combination of the acid treatment and desilication treatment made all the Brønsted acid sites of the final desilicated mesoporous mordenite catalysts accessible to the basic probe molecule and, therefore, also accessible to the hydrocarbons present in our reaction feedstock.

The metal component was loaded onto the zeolite catalyst, which includes desilicated mesoporous mordenite and the desilicated mesoporous mordenite mixed with ZSM-5 via the incipient wetness method. The metal loaded catalyst contained approximately 0.3 wt. % rhenium (Re). The physicochemical properties of these samples are listed in Table 4, infra, for the six catalyst samples as described previously. The reference catalyst, the rhenium loaded MOR or "Re MOR", was included in all tables for comparison purposes.

TABLE 4

Physicochemical Properties of the Zeolite Catalyst with Rhenium.

| Sample | ICP-MS | | $S_{Bet}$ (m²/g) | $S_{micro}$ (m²/g) | $S_{Ext}$ (m²/g) | $V_{micro}$ (cm³/g) | $V_{meso}$ (cm³/g) | $V_{micro}/V_{meso}$ |
|---|---|---|---|---|---|---|---|---|
| | Si/Al | Re (wt. %) | | | | | | |
| Re MOR | 8.9 | 0.32 | 429 | 408 | 21 | 0.200 | 0.027 | 7.41 |
| Re Cat. 1 | 7.1 | 0.35 | 529 | 369 | 160 | 0.182 | 0.158 | 1.15 |
| Re Cat. 2 | 30.1 | 0.28 | 541 | 366 | 175 | 0.183 | 0.174 | 1.05 |
| Re Cat. 3 | 13.7 | 0.28 | 534 | 322 | 212 | 0.155 | 0.230 | 0.674 |
| Re Cat. 4 | 35.7 | 0.29 | 546 | 318 | 228 | 0.153 | 0.239 | 0.640 |
| Re Cat. 5 | 15.9 | 0.28 | 520 | 335 | 185 | 0.163 | 0.223 | 0.731 |
| Re Cat. 6 | 40.6 | 0.28 | 535 | 352 | 183 | 0.171 | 0.224 | 0.763 |

In these examples, the Re content was measured by ICP-MS and was close to the target (0.3 wt. %), and the incorporation of the metal resulted in a small reduction of BET surface area and micro and mesopore volume of the zeolite. However, this decrease was less for the more mesoporous mordenite (Cat. 4 and Cat. 6), which was obtained by mordenite dealuminated using acid treatments 2 and 3.

The addition of Re resulted in a reduction of the total and strong Brønsted acid site density in the case of the reference microporous mordenite, as shown in Table 5, where total Brønsted acid sites are those able to retain pyridine at 150° C. (B150) and strong Brønsted acid sites are those able to retain pyridine at the highest desorption temperature of 350° C. (B350). Acid sites B150 and B350 decreased when adding rhenium, and the proportion of strong sites, given as B350/B150, did not follow a single trend. There was an increase of the proportion of strong acid sites in the case of the non-modified MOR and the Re MOR. In the case of the mesoporous mordenite, the proportion of strong sites varied between 40% and 50%.

TABLE 5

Acidic Properties of Mordenite Compounds

| Sample | Brønsted Acidity (u.a.) | | | | Lewis Acidity (u.a.) | | |
|---|---|---|---|---|---|---|---|
| | B150 | B250 | B350 | B350/B150 | L150 | L250 | L350 |
| Re MOR | 400 | 363 | 299 | 0.75 | 65 | — | — |
| Re Cat. 1 | 420 | 292 | 130 | 0.31 | 239 | 185 | 128 |
| Re Cat. 2 | 134 | 121 | 49 | 0.37 | 36 | 34 | 23 |
| Re Cat. 3 | 282 | 188 | 124 | 0.44 | 227 | 124 | 124 |
| Re Cat. 4 | 145 | 102 | 64 | 0.44 | 51 | 31 | 30 |

TABLE 5-continued

Acidic Properties of Mordenite Compounds

| Sample | Brønsted Acidity (u.a.) | | | | Lewis Acidity (u.a.) | | |
|---|---|---|---|---|---|---|---|
| | B150 | B250 | B350 | B350/B150 | L150 | L250 | L350 |
| Re Cat. 5 | 161 | 144 | 86 | 0.53 | 184 | 126 | 93 |
| Re Cat. 6 | 107 | 92 | 43 | 0.40 | 33 | 20 | 15 |

Catalytic Conversion of a Model Feed in a High-Throughput Fixed Bed Reaction System Catalytic tests with the model feed were performed in a high-throughput reaction system consisting of 16 continuous fixed-bed parallel microreactors. The liquid feed was composed of para-methylethylbenzene (30 wt. %) and 1,2,4-trimethylbenzene (70 wt. %). The catalytic experiments were carried out under the following conditions: 20 bar total pressure, hydrogen/hydrocarbon molar ratio of 8.5, reaction time of 16 h, and WHSV=10 h$^{-1}$. The amount of catalyst (particle size 0.2-0.4 mm) in each fixed-bed microreactor was 125 mg diluted with CSi to a total bed volume of 2.0 ml.

The zeolite catalysts with rhenium (0.3 wt. % Re) were tested in this high-throughput reaction system consisting of 16 continuous fixed-bed parallel microreactors for a first screening of their activity, selectivity to xylenes and stability towards deactivation. The conversion of MEB, TMB, and the overall conversion (obtained as the sum of the two former) and yields to the main products as a result of Re Cat. 1 and Re Cat. 2 are presented in FIGS. 2A-3C. In each of the FIGS. 2A-7C, comparative examples of unmodified mordenite, Re MOR, and the ATA-21, were compared to the desilicated mesoporous mordenite. The activity and yield curves were obtained at four different temperatures, 350° C., 375° C., 400° C., and again 350° C. The results, shown in FIG. 2A, indicated that the increase of mesopores after a single nitric acid treatment (acid treatment 1 applied to Cat. 1 and Cat. 2) improved the accessibility of the zeolite. As a result, there was an increase to the dealkylation and the transalkylation capacity of the catalyst in comparison to the comparative catalyst Re MOR. The increased capacity of dealkylation and transalkylation was especially apparent when the catalyst washed with the ammonium solution, Cat. 1, was compared to the rhenium loaded comparative catalyst, Re MOR.

Figure 2A:
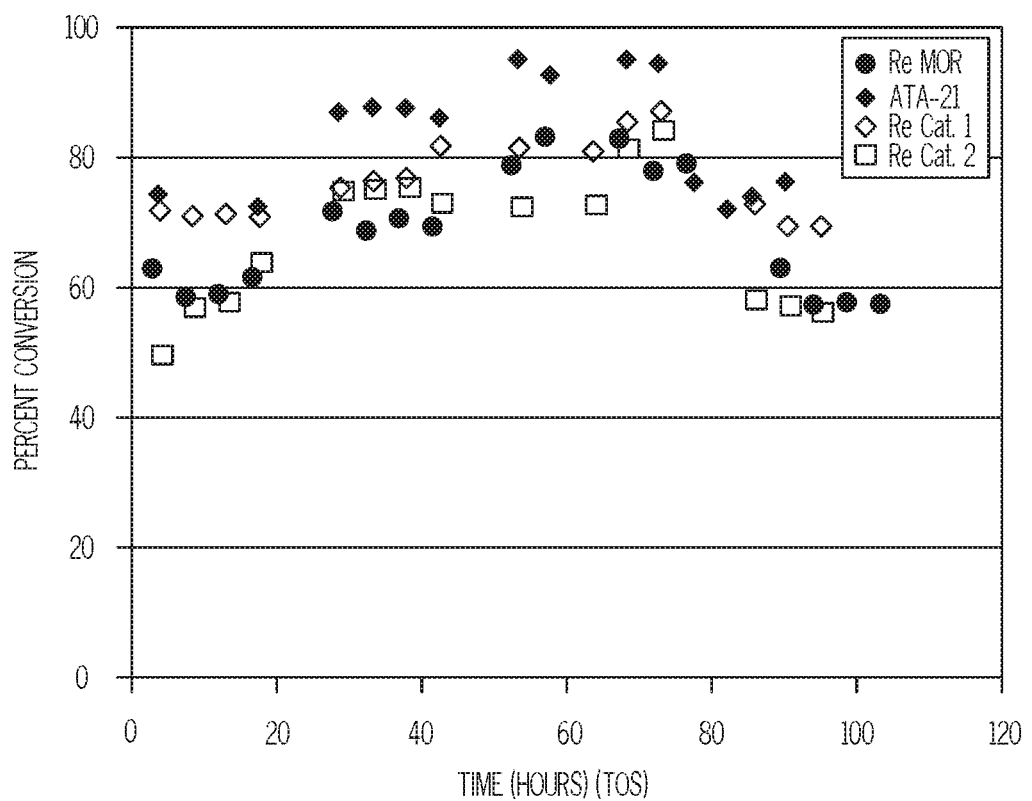
FIG. 2A is a graph, in which each data point represents the percent conversion as a function of time of methylethylbenzene (MEB) when a heavy reformate feed stream reacts with a particular catalyst. The catalysts are described in detail in the Examples section infra. The solid diamonds represent the commercially available mordenite base compound ATA-21, the circles represent Re MOR, the unfilled diamonds represent Re Cat. 1, and the unfilled squares represent Re Cat. 2.
Figure 2B:
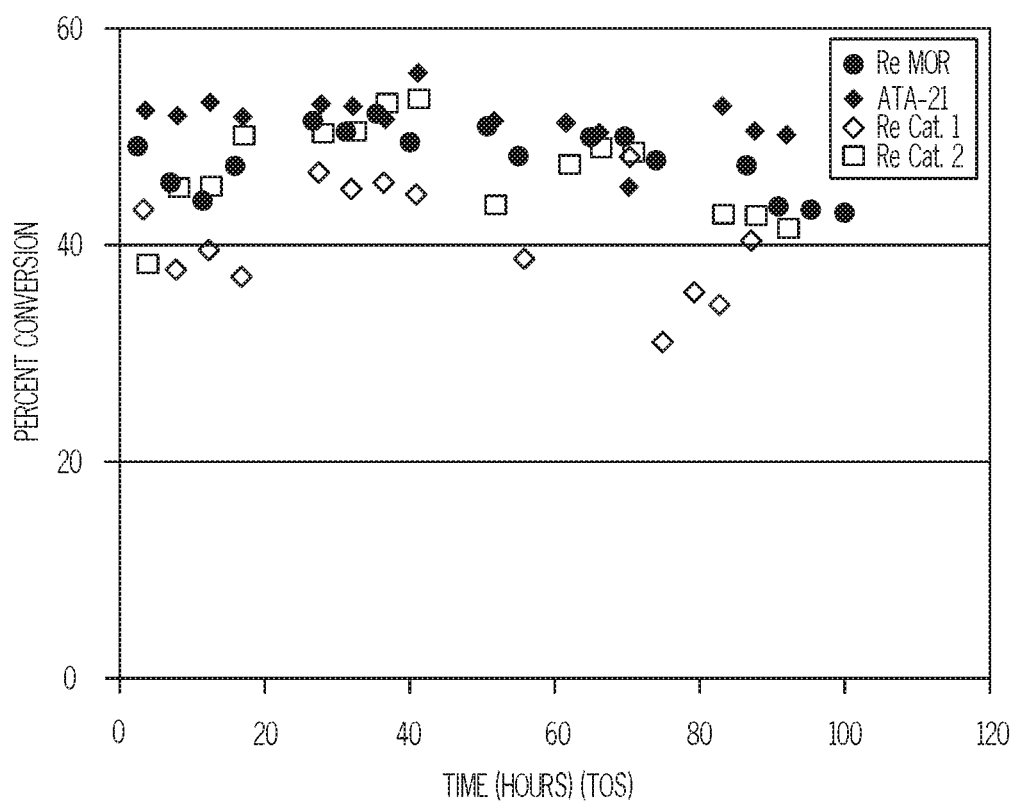
FIG. 2B is a graph, in which each data point represents the percent conversion as a function of time of trimethylbenzene (TMB) when a feed stream reacts with the particular catalysts, as described in the preceding paragraph.
Figure 2C:
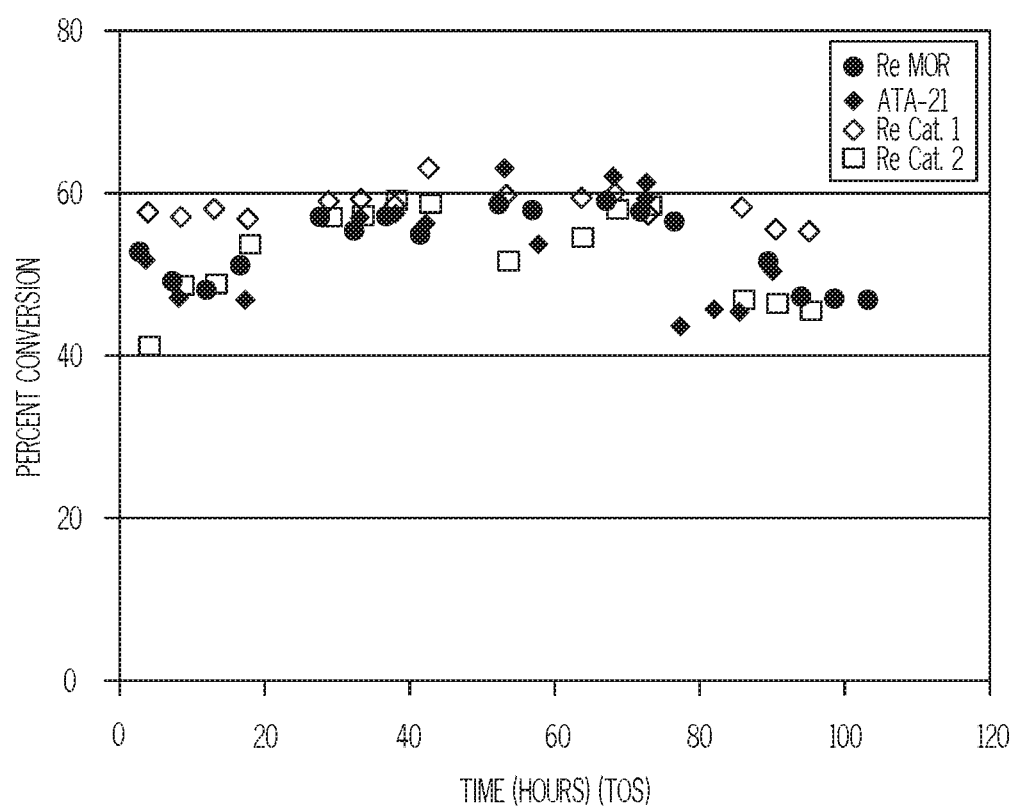
FIG. 2C is a graph in which each data point represents the percent conversion as a function of time of the overall conversion of TMB and MEB when a feed stream reacts with the particular catalysts, as described for FIG. 2A supra.

In FIGS. 2A-2C, the results showed that Re Cat. 2, obtained after washing with oxalic acid, presented an activity very similar to the commercial non modified mordenite, Re MOR. No significant deactivation was observed throughout the experiment for any of the catalysts compared. When comparing the product distribution in FIGS. 3A-3C, the differences when compared to Re MOR were not large. Re Cat. 1 yielded a similar amount of xylenes when compared to the reference mordenite or Re Cat. 2. The amount of aromatic molecules with 10 carbons (A$_{10}$) was similar for both desilicated samples, and similar to the one obtained with Re MOR and the ammonium washed sample, Re Cat. 1, which gave the largest TMB conversion.

Figure 3A:
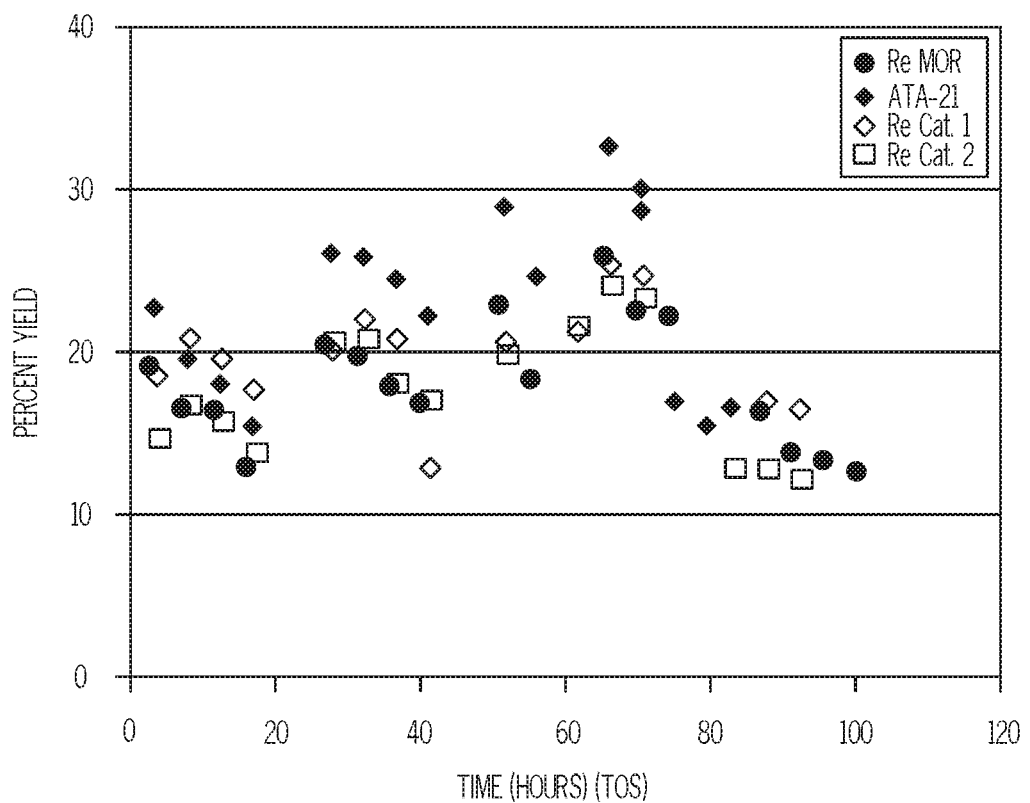
FIG. 3A is a graph in which each data point represents the percent yield as a function of time of xylenes yielded from a hydrocarbon when a feed stream reacts with the particular catalysts, as described for FIG. 2A supra.
Figure 3B:
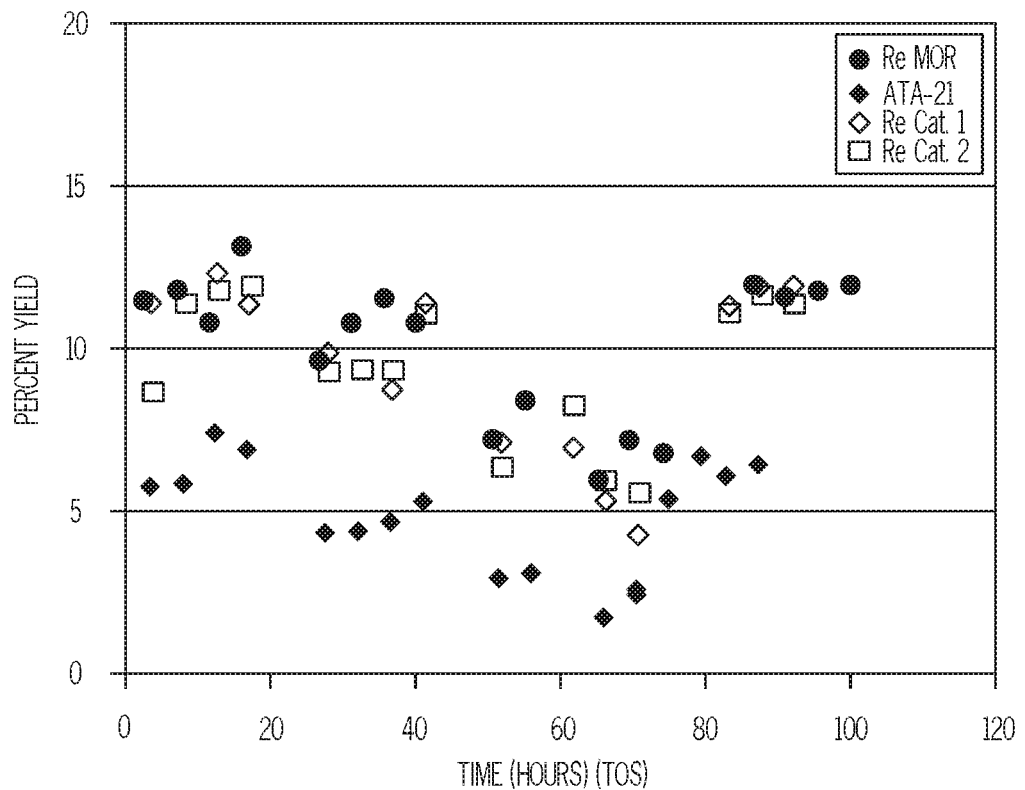
FIG. 3B is a graph in which each data point represents the percent yield of remaining aromatics having 10 carbons in the molecule ($A_{10}$) as a function of time when a feed stream reacts with the particular catalysts, as described for FIG. 2A supra.
Figure 3C:
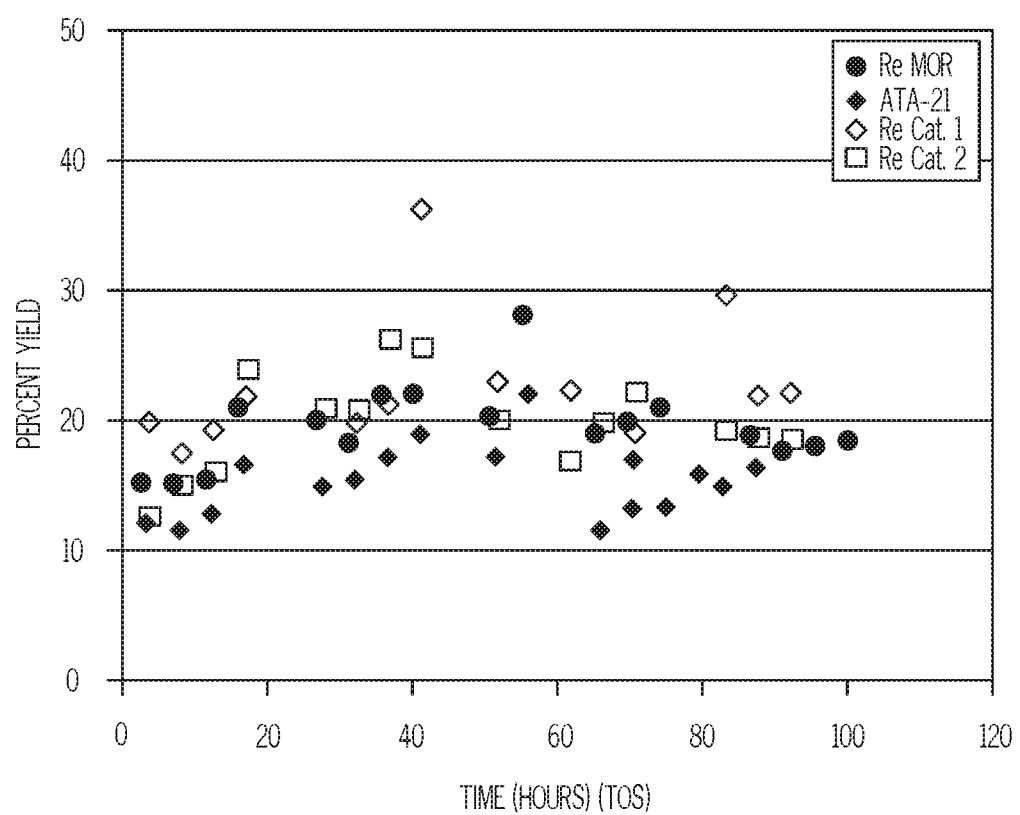
FIG. 3C is a graph in which each data point represents the percent yield of remaining aromatics having more than 10 carbons in the molecule ($A_{10+}$) as a function of time when a feed stream reacts with the particular catalysts, as described for FIG. 2A supra.
Figure 4A:
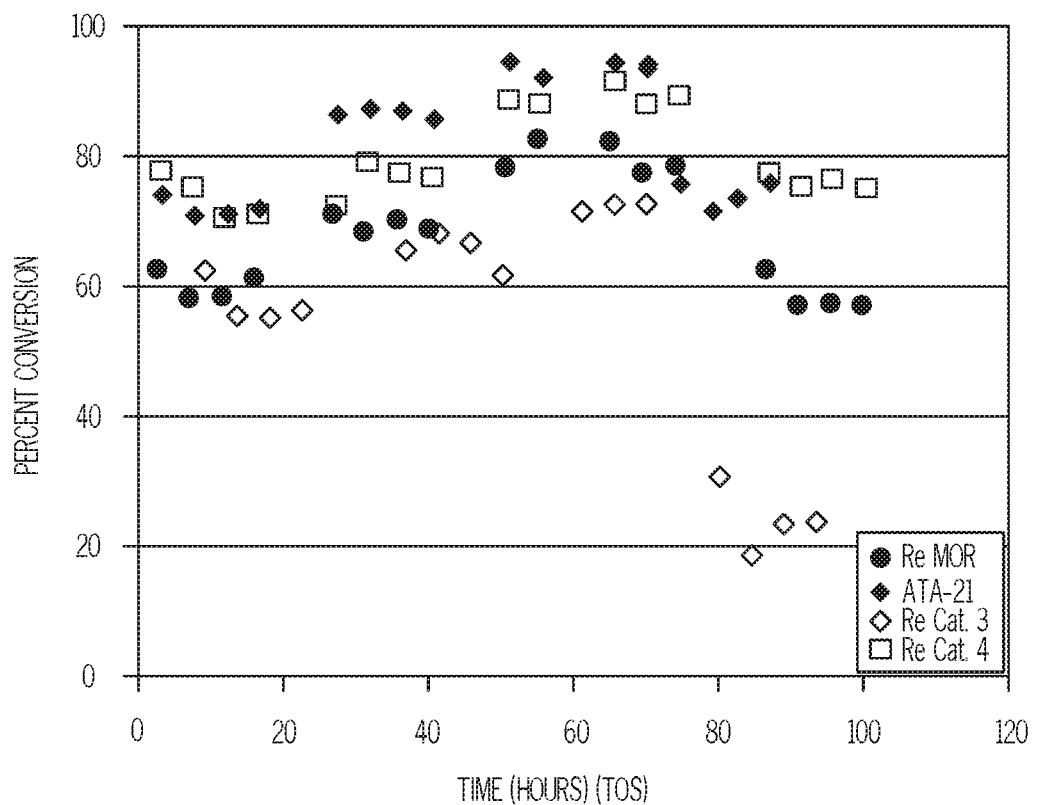
FIG. 4A is a graph in which each data point represents the percent conversion of MEB as a function of time when a feed stream reacts with a particular catalyst: the solid diamonds represent the commercially available mordenite base compound ATA-21, the circles represent Re MOR, the unfilled diamonds represent Re Cat. 3, and the unfilled squares represent Re Cat. 4.
Figure 4B:
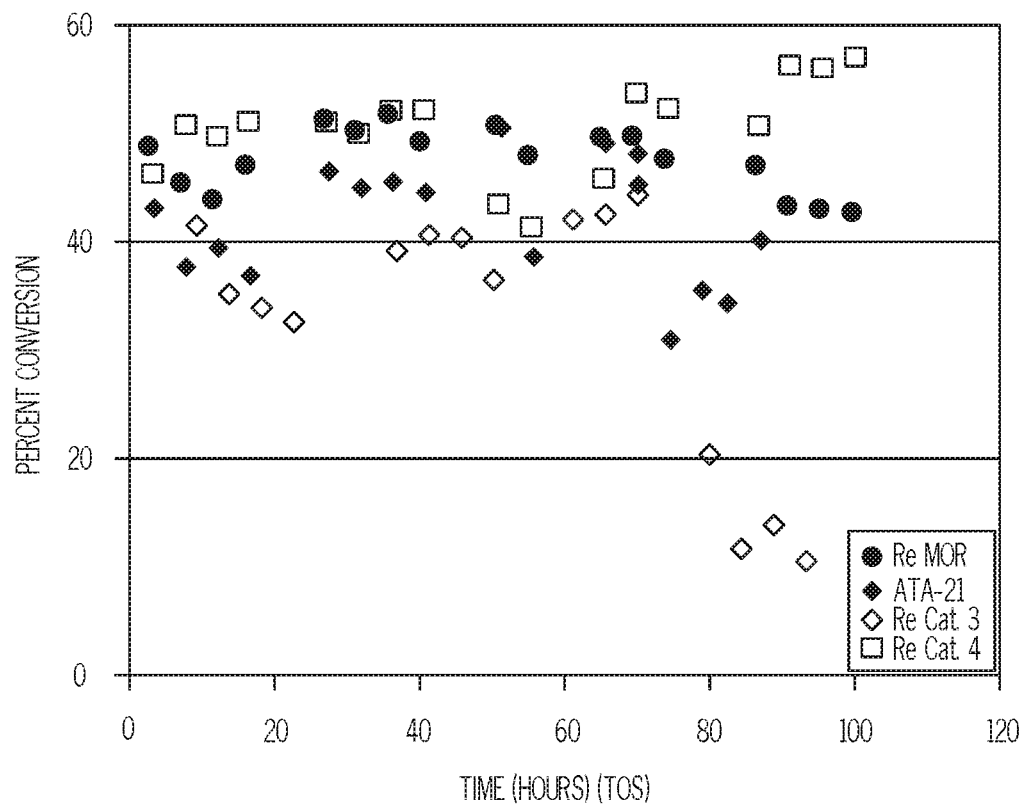
FIG. 4B is a graph in which each data point represents the percent conversion of TMB as a function of time when a feed stream reacts with the particular catalysts, as described in the preceding paragraph.
Figure 4C:
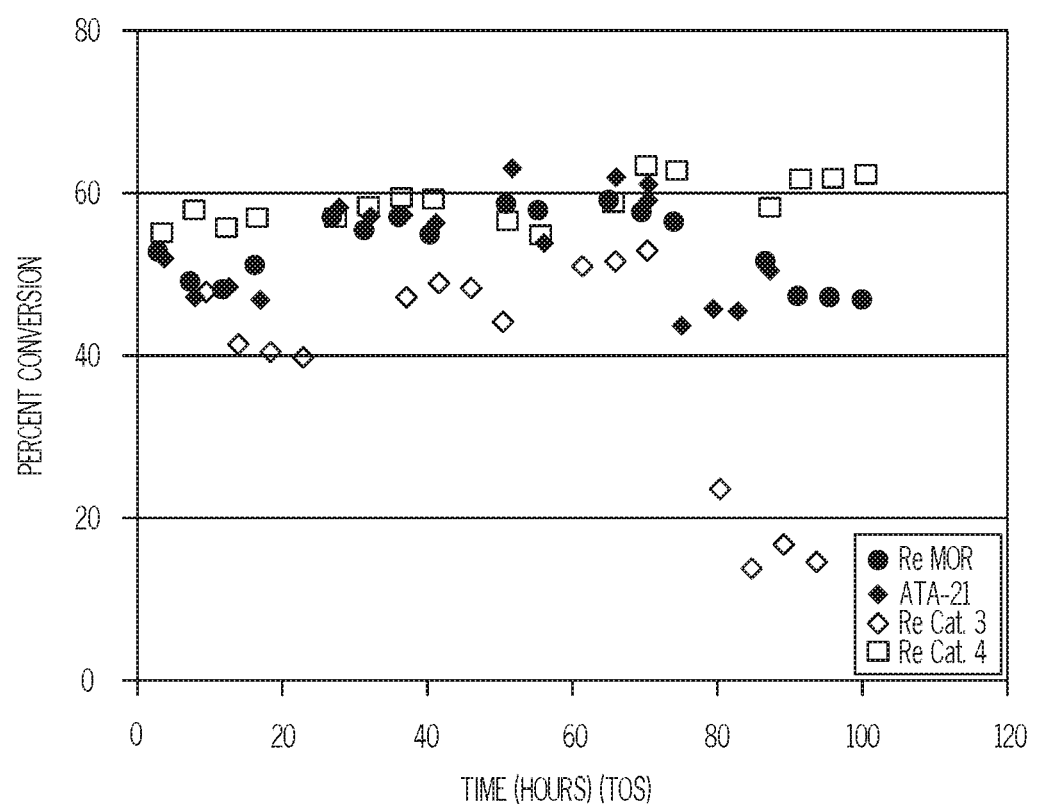
FIG. 4C is a graph in which each data point represents the percent conversion of the overall conversion of TMB and MEB as a function of time when a feed stream reacts with the particular catalysts, as described for FIG. 4A supra.
Figure 5A:
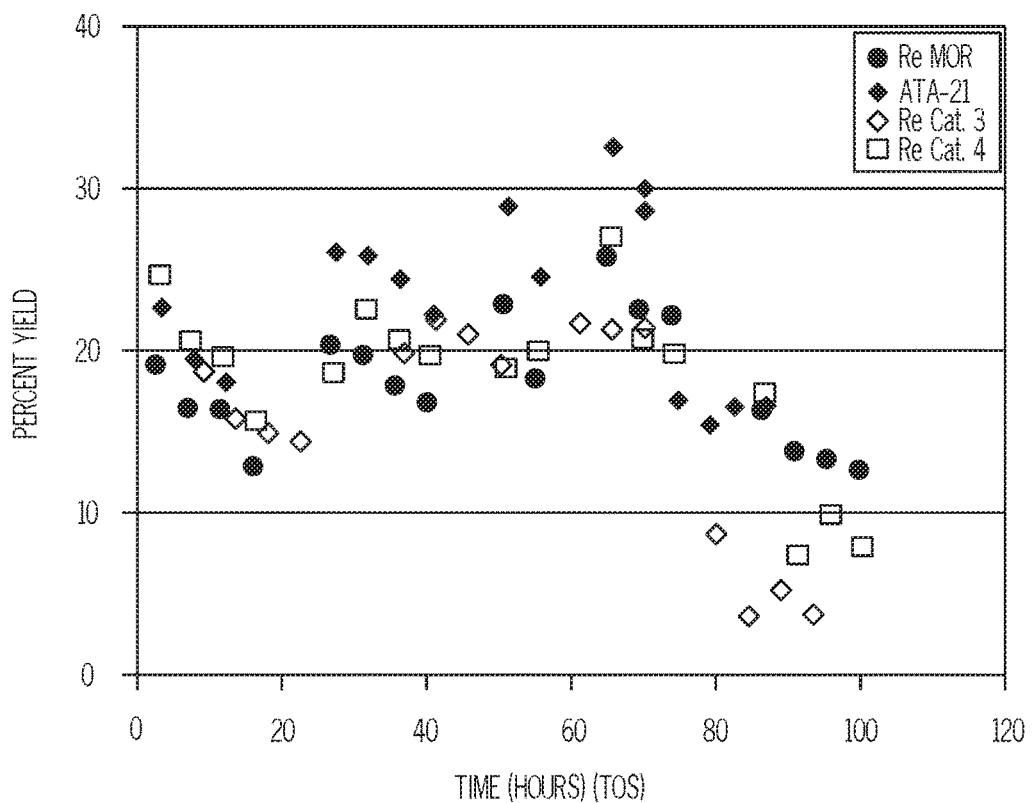
FIG. 5A is a graph in which each data point represents the percent yield of xylene remaining as a function of time when a feed stream reacts with the particular catalysts, as described for FIG. 4A supra.
Figure 5B:
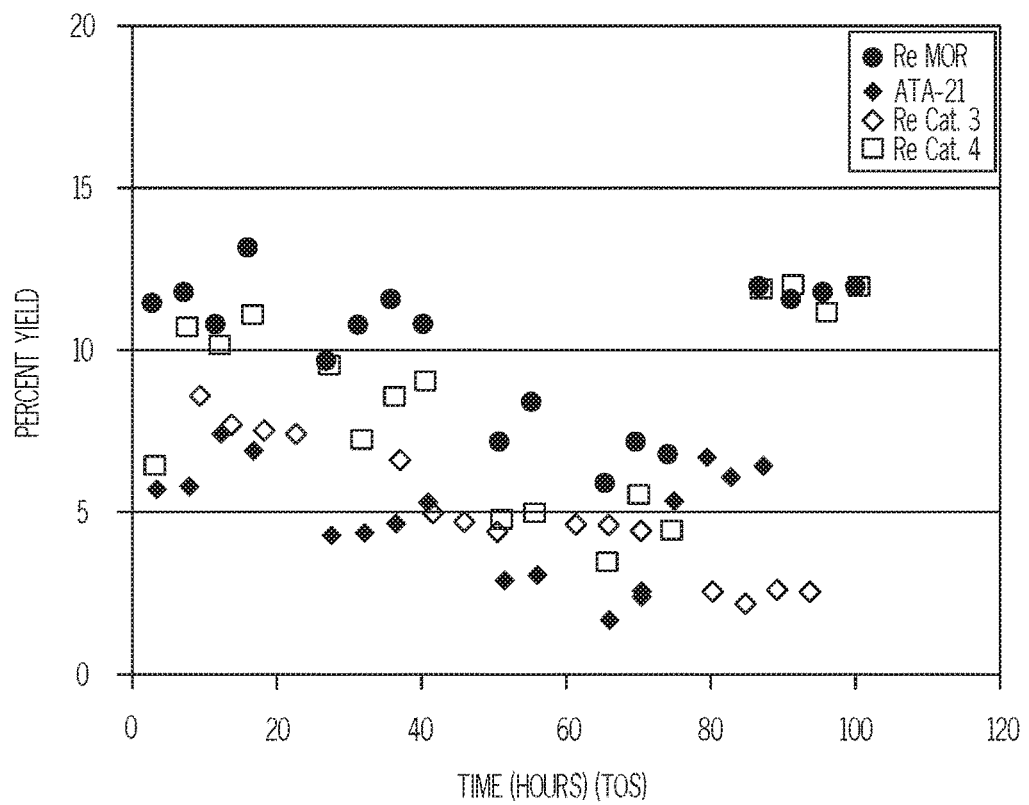
FIG. 5B is a graph in which each data point represents the percent yield of remaining $A_{10}$ as a function of time when the feed stream reacts with the particular catalysts, as described for FIG. 4A supra.
Figure 5C:
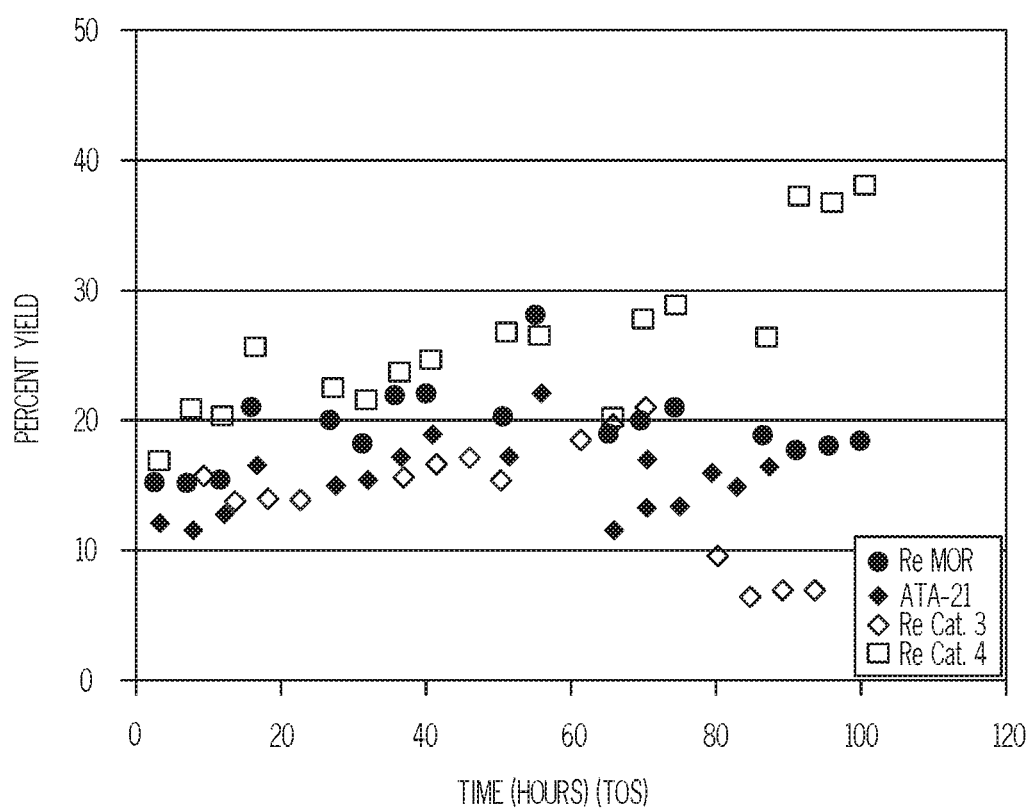
FIG. 5C is a graph in which each data point represents the percent yield of remaining $A_{10+}$ as a function of time when the feed stream reacts with the particular catalysts, as described for FIG. 4A supra.

The results shown in FIGS. 3A-3C indicated that as the accessibility was increased by increasing the mesoporosity, and the overall acidity was preserved by limiting framework dealumination (Re Cat. 1). The conversion was improved as compared to the microporous Re MOR, and the yield to xylenes is maintained as shown in FIG. 3A. Re Cat. 1 and Re Cat. 2 do not contain a medium pore zeolite as a dealkylation component, but they provide comparable results than those of ATA-21.

In FIGS. 4A-5C, the activity and product yields of the Re catalysts from MOR-A treated with the acid treatment 2 (Re Cat. 3 Re Cat. 4) were charted and compared with ATA-21 and Re MOR. In comparison, the activity of the mesoporous sample after oxalic acid treatment, Re Cat. 4, is greater than that of Re Cat. 3, the Re MOR reference, and ATA-21. Re Cat. 4 was slightly less active for MEB conversion than ATA-21, but converts significantly more TMB. Regarding the production of xylenes, Re Cat. 4 was comparable to Re MOR, due to a larger formation of heavy aromatics (A$_{10+}$).

Figure 6A:
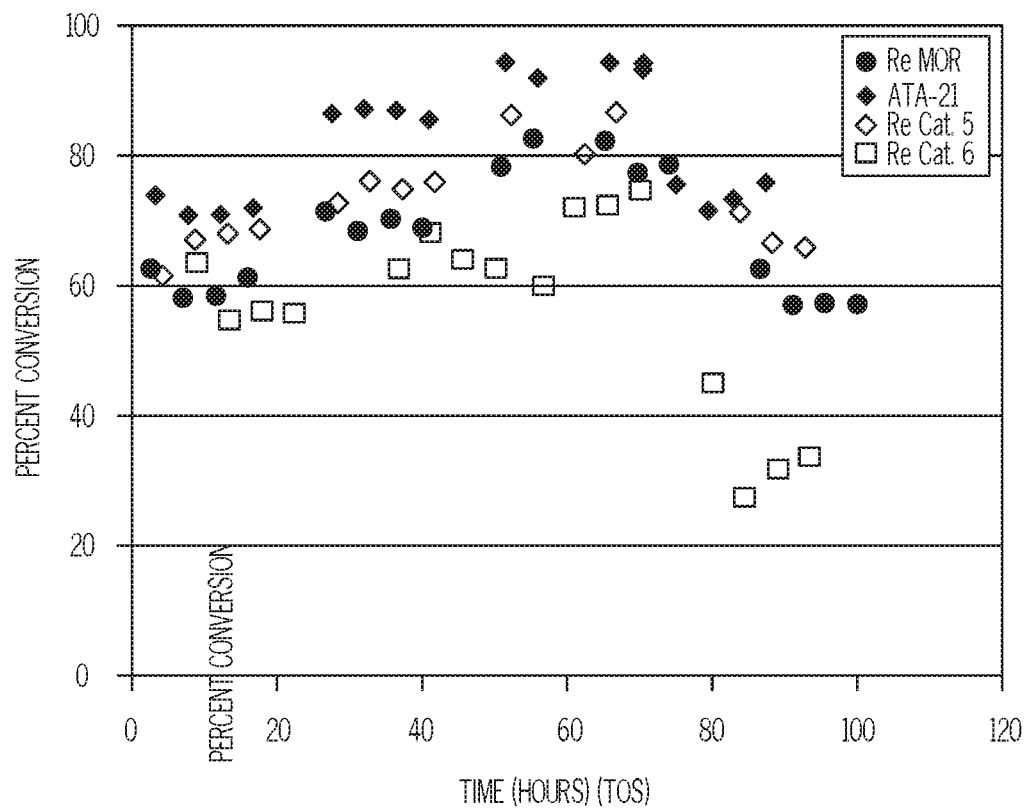
FIG. 6A is a graph in which each data point represents the percent conversion as a function of time of MEB when a feed stream reacts with a particular catalyst: solid diamonds represent the commercially available mordenite base compound ATA-21, the circles represent Re MOR, the unfilled diamonds represent Re Cat. 5, and the unfilled squares represent Re Cat. 6.
Figure 6B:
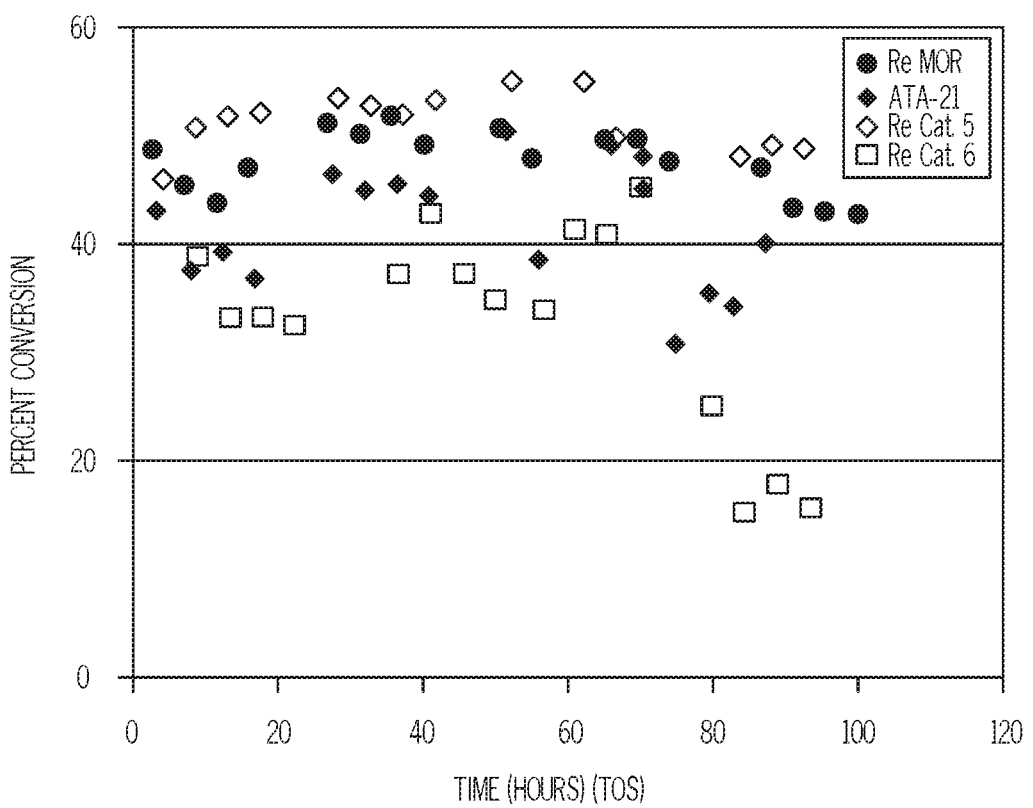
FIG. 6B is a graph in which each data point represents the percent conversion as a function of time of TMB when a feed stream reacts with the particular catalysts, as described in the preceding paragraph.
Figure 6C:
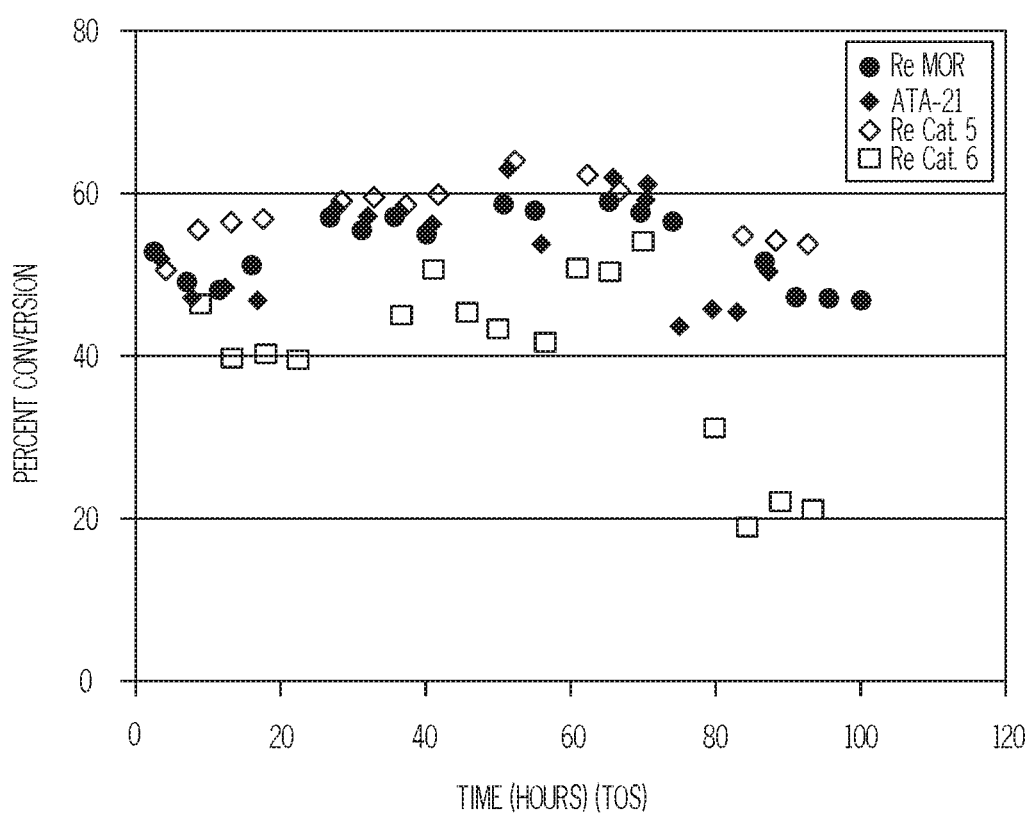
FIG. 6C is a graph in which each data point represents the percent conversion as a function of time of the overall conversion when a feed stream reacts with the particular catalysts, as described for FIG. 6A supra.
Figure 7A:
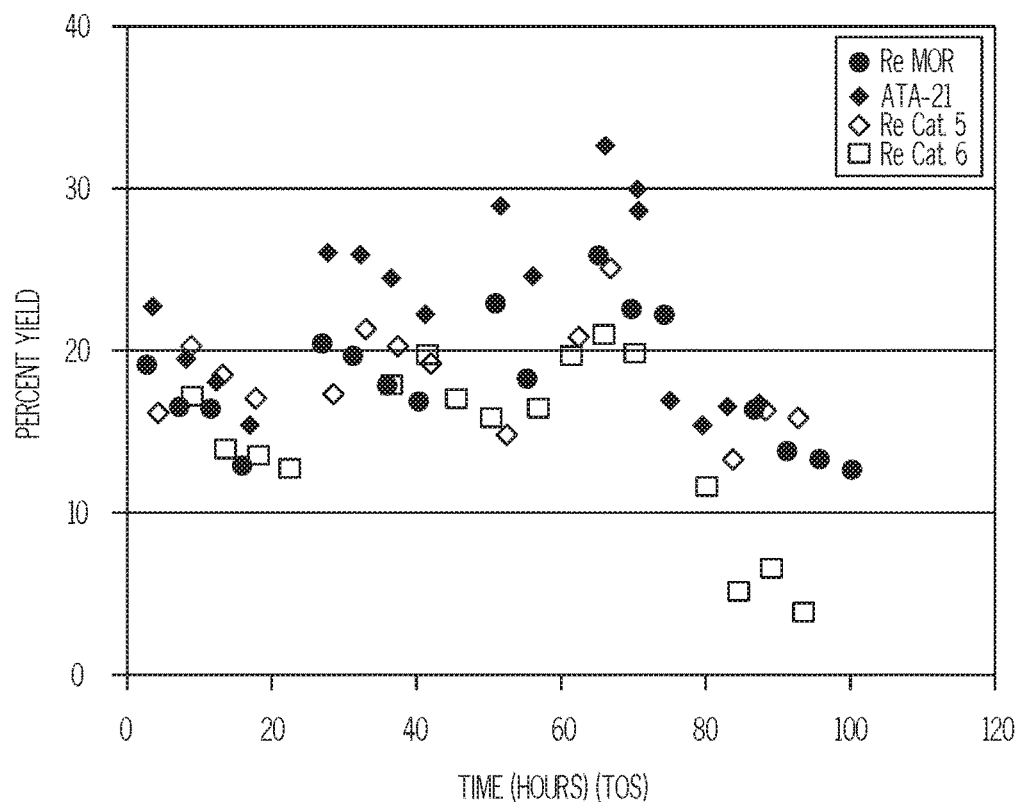
FIG. 7A is a graph in which each data point represents the percent yield of xylene remaining as a function of time when a feed stream reacts with the particular catalysts, as described for FIG. 6A supra.
Figure 7B:
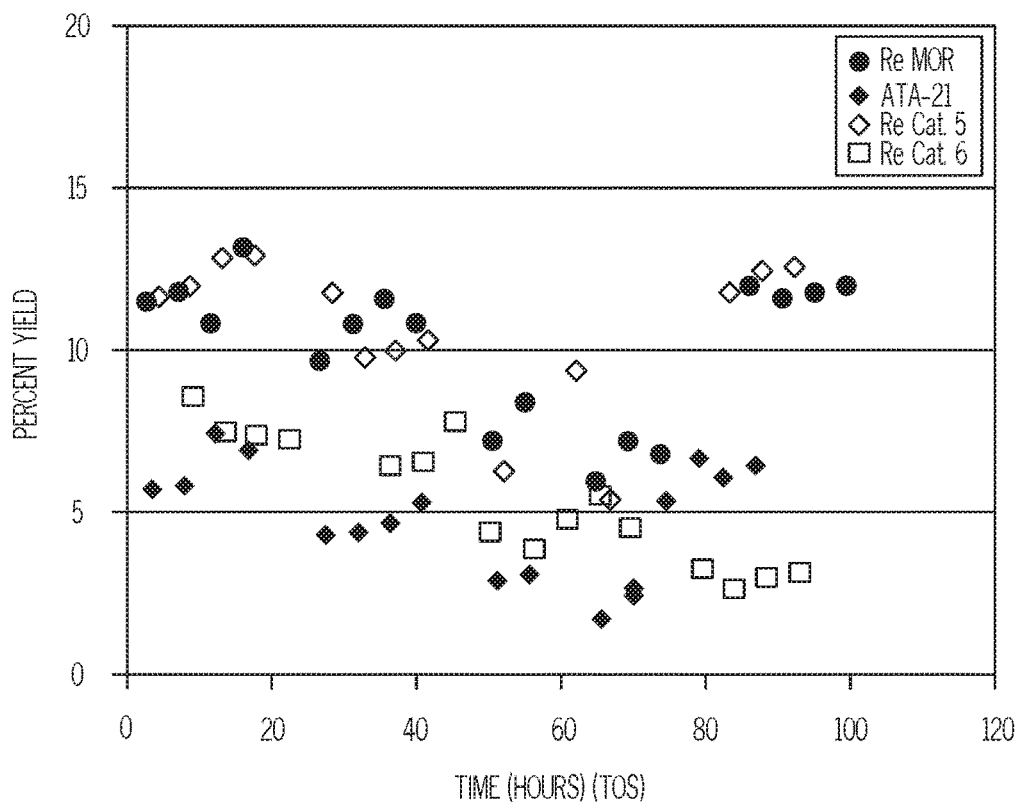
FIG. 7B is a graph in which each data point represents the percent yield of remaining $A_{10}$ aromatics as a function of time when a feed stream reacts with the particular catalysts, as described for FIG. 6A supra.
Figure 7C:
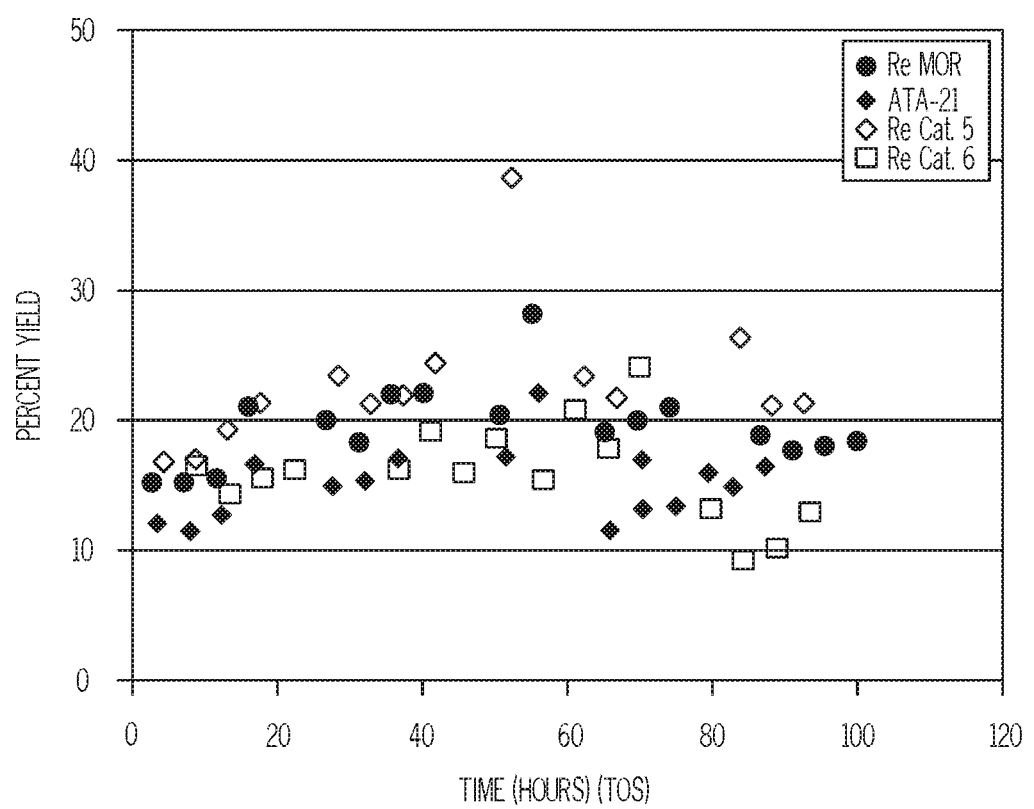
FIG. 7C is a graph in which each data point represents the percent yield of remaining $A_{10+}$ as a function of time when the feed stream reacts with the particular catalysts, as described for FIG. 6A supra.

The results obtained with the catalysts produced by desilication of the most dealuminated sample (Re Cat. 5 and Re Cat. 6) are shown in FIGS. 6-7. Re Cat. 5 was more active than Re MOR and Re Cat. 6, and converted more MEB and TMB to xylenes. This sample created a yield of xylenes greater than reference Re MOR at low temperature (350° C.). The reason for the better performance of this catalyst as compared to the other mesoporous mordenite based samples is the lesser production of heavy aromatics (A$_{10+}$).

Catalytic Conversion of an Industrial Heavy Reformate Feed in Conventional Fixed Bed Reactor The industrial heavy reformate (HR) was processed in a fixed-bed stainless-steel tubular reactor having a 10.5 mm i.d. and 20 cm length. The reactor was charged with the catalyst (particle size of 0.2 to 0.4 mm) diluted with SiC up to a total bed volume of 5.8 ml. The reaction was performed at 20 bar, a temperature of 350° C., 375° C. and 400° C., weight hourly space velocity (WHSV) of 10 per hour (hr$^{-1}$), (hydrogen/hydrocarbon) H$_2$/HC feed of 4. Re Cat. 4 and Re Cat. 1 were tested in a conventional fixed bed reactor as catalysts in conversion of the industrial heavy reformate (HR) feed. Re Cat. 4 had a larger mesopore volume and was the most active for conversion of the model feed. However, Re Cat. 4 produced large yields of the heavy aromatic fraction A$_{10+}$. Therefore, Re Cat. 4, besides being tested alone, was tested after mixing in a 60:40 (wt/wt) ratio with a rhenium loaded ZSM-5 (Re ZSM-5). This catalyst was named as "Re Cat. 4+Re ZSM-5". There were three comparative catalysts studied: ATA-21, a commercially available unmodified mordenite based catalyst, Re MOR, and Re MOR+Re ZSM-5, a catalyst created by mixing Re MOR with Re ZSM-5 in a 60:40 (wt/wt) ratio. In these examples, the Re ZSM-5 component was the same component used in combination with the mesoporous mordenite.

The catalysts used in these examples were prepared by loading the rhenium on the individual zeolite, mesoporous mordenite and ZSM-5, and mixing the Re-loaded zeolites as a powder (dry physical mixing).

Figure 8A:
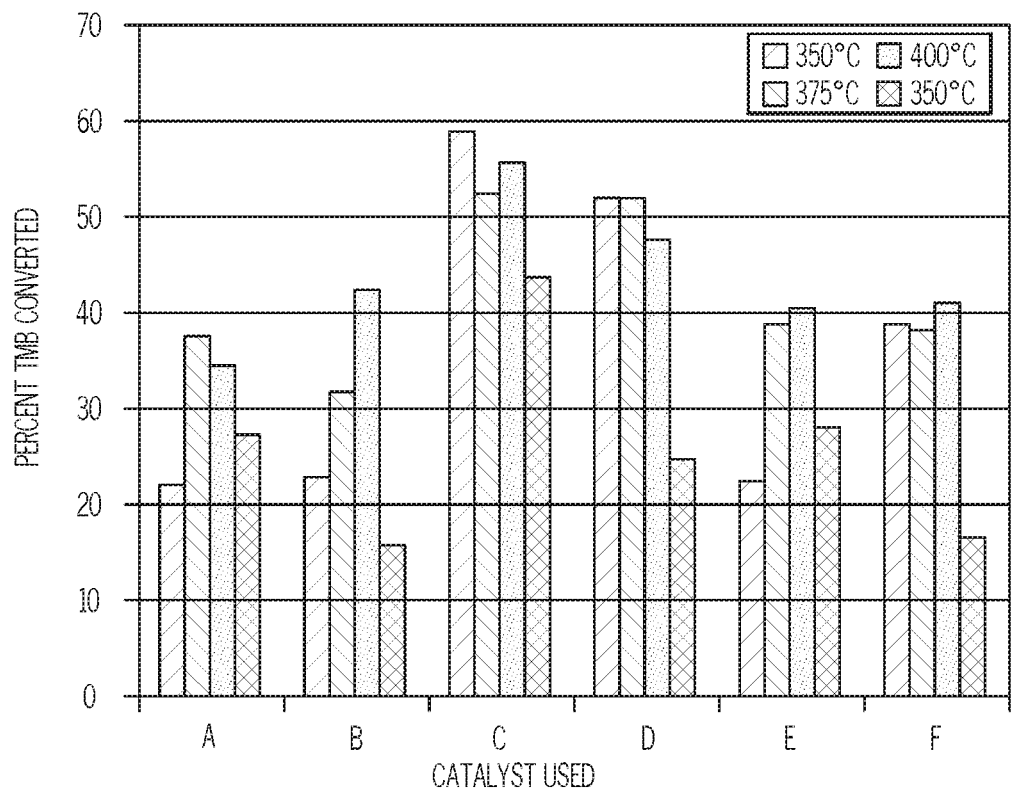
FIG. 8A is a bar chart of the percent of TMB converted as a function of temperature when an industrial heavy reformate feed stream reacts with a catalyst. Seven different catalysts are studied at four different temperatures: 350° C., 375° C., 400° C., and again at 350° C. as listed from left to right in the chart. The catalysts, as described in the Examples section infra, are designated as follows: "A" is ATA-21, "B" is Re MOR, "C" is Re Cat. 4, "D" is Re Cat. 1, "E" is Re MOR+ZSM-5, and "F" is Re Cat. 4+Re ZSM-5.
Figure 8B:
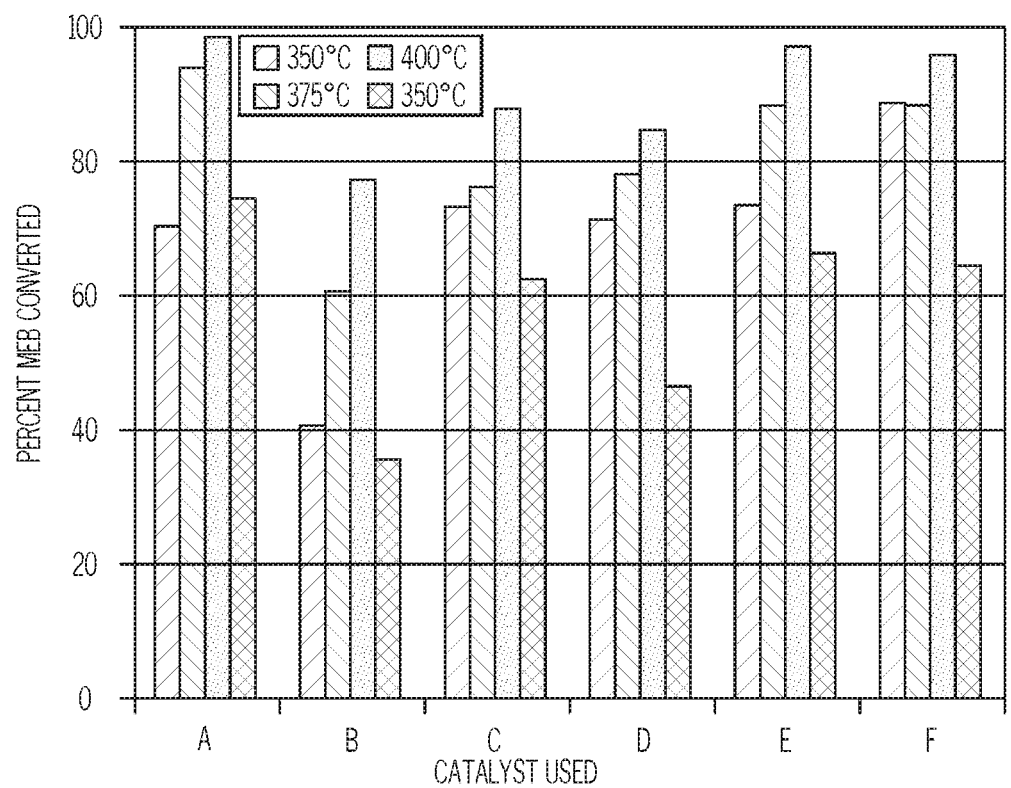
FIG. 8B is a bar chart of the percent of the MEB converted as a function of temperature when a feed stream reacts with a catalyst; the reaction conditions and catalyst are the same as that described in the preceding paragraph.
Figure 8C:
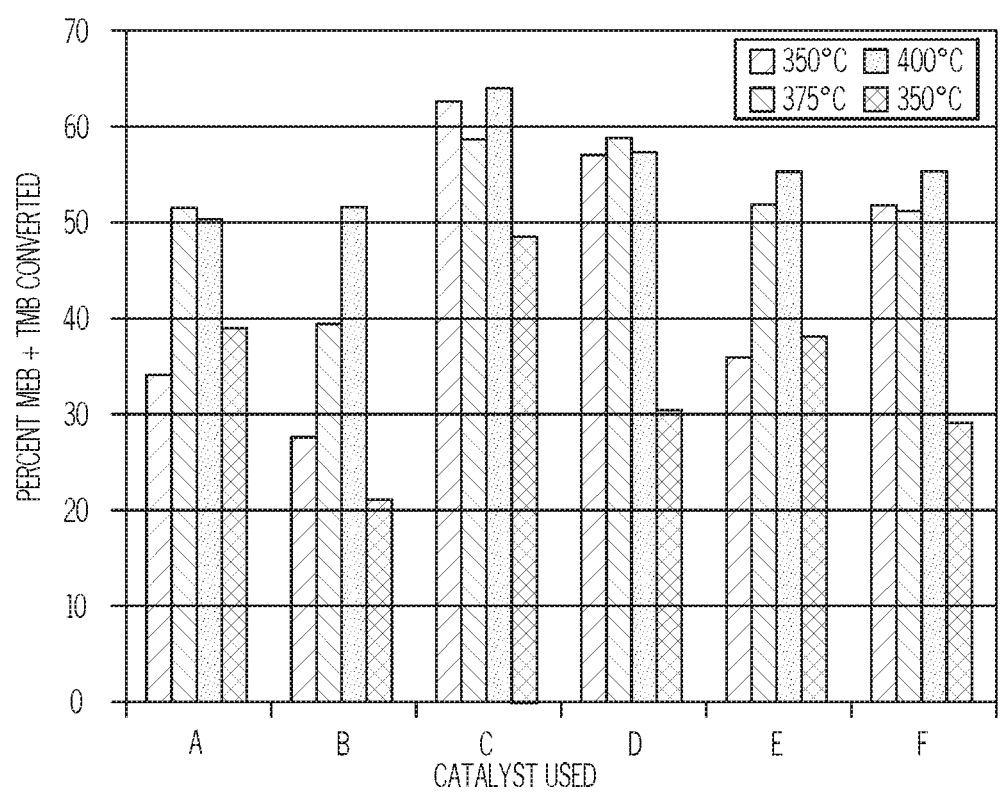
FIG. 8C is a bar chart of the percent of MEB and TMB converted as a function of temperature when a feed stream reacts with a catalyst; the reaction conditions and catalyst are the same as that described for FIG. 8A supra.

In FIGS. 8A-8C, the MEB (dealkylation), TMB (transalkylation) and overall conversion (MEB and TMB) are presented for the different catalysts detailed in the preceding paragraph. In good agreement with the results obtained in the Spider reactor, the two desilicated samples, Re Cat. 1 and Re Cat. 4, are more active for both, dealkylation and transalkylation reactions, as compared to the microporous mordenite Re MOR. The TMB conversion yielded by Re Cat. 4 and Re Cat. 1 was greater than that of the comparative samples (Re MOR and ATA-21), and the percent of MEB conversion by Re Cat. 4 and Re Cat. 1 surpassed that of the Re MOR.

Thus, the overall activity of the desilicated mesoporous mordenite catalysts was greater than that of any of the other catalysts compared here, especially the activity of the catalyst prepared by the acid treatment 2 followed by the desilication treatment and an oxalic acid wash (Re Cat. 4).

Figure 9A:
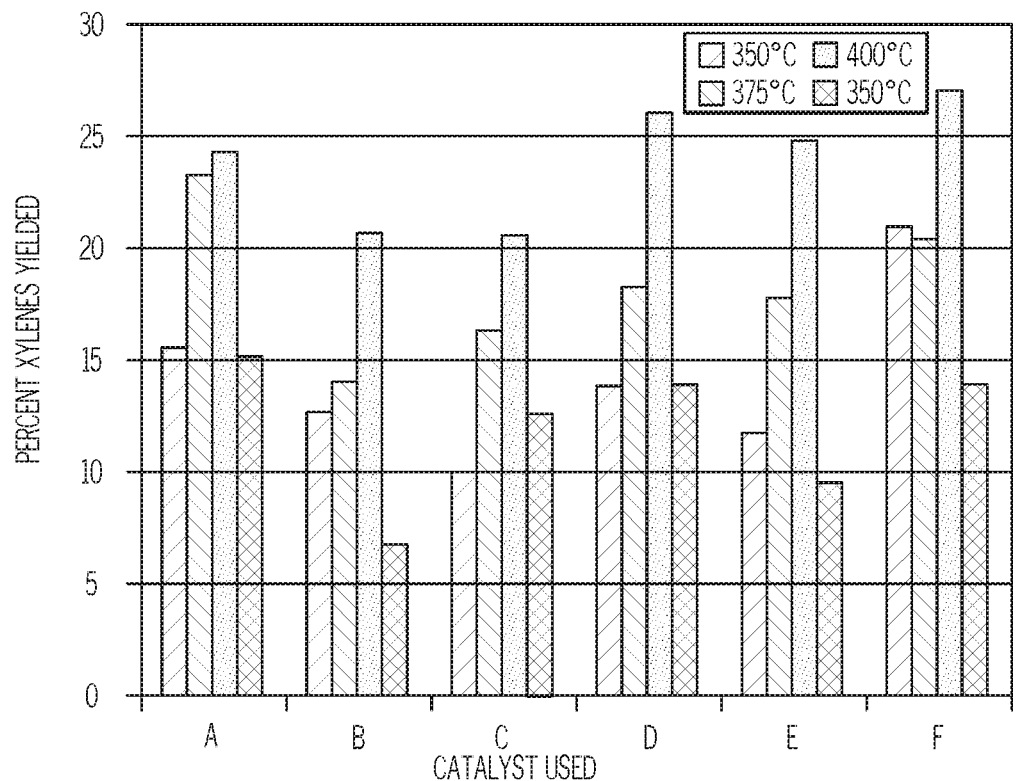
FIG. 9A is a bar chart of the percent of xylenes yielded as a function of temperature when a feed stream reacts with a catalyst; the reaction conditions and catalyst are the same as that described for FIG. 8A supra.
Figure 9B:
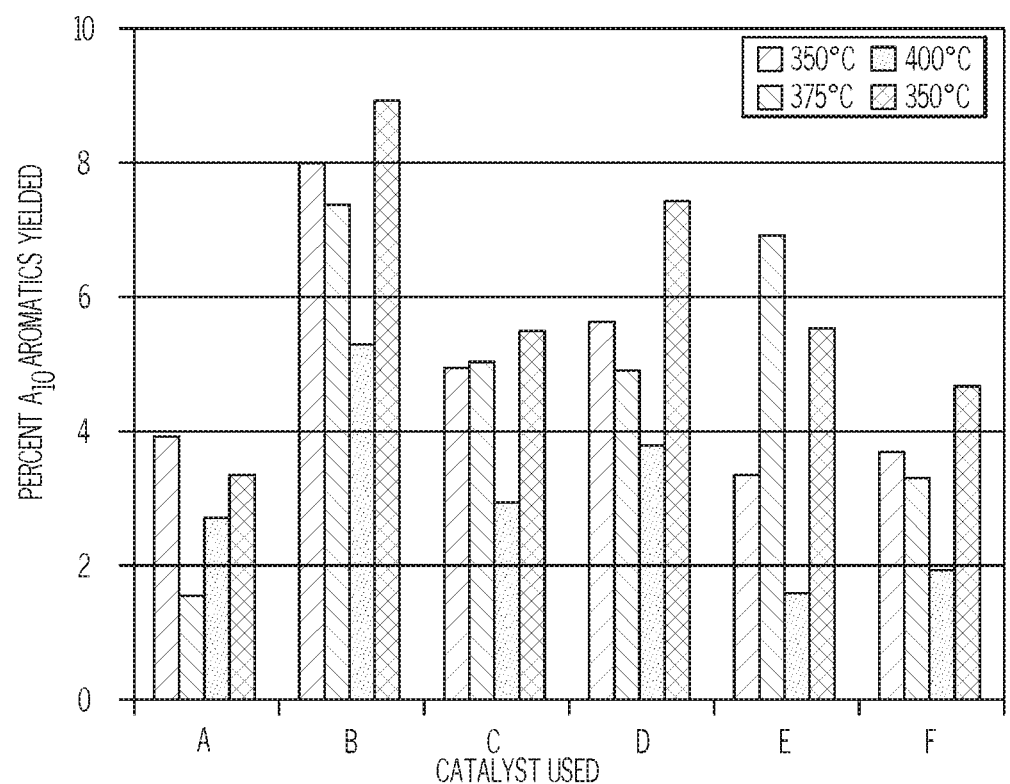
FIG. 9B is a bar chart of the percent of $A_{10}$ aromatics yielded of as a function of temperature when a feed stream reacts with a catalyst; the reaction conditions and catalyst are the same as that described for FIG. 8A supra.
Figure 9C:
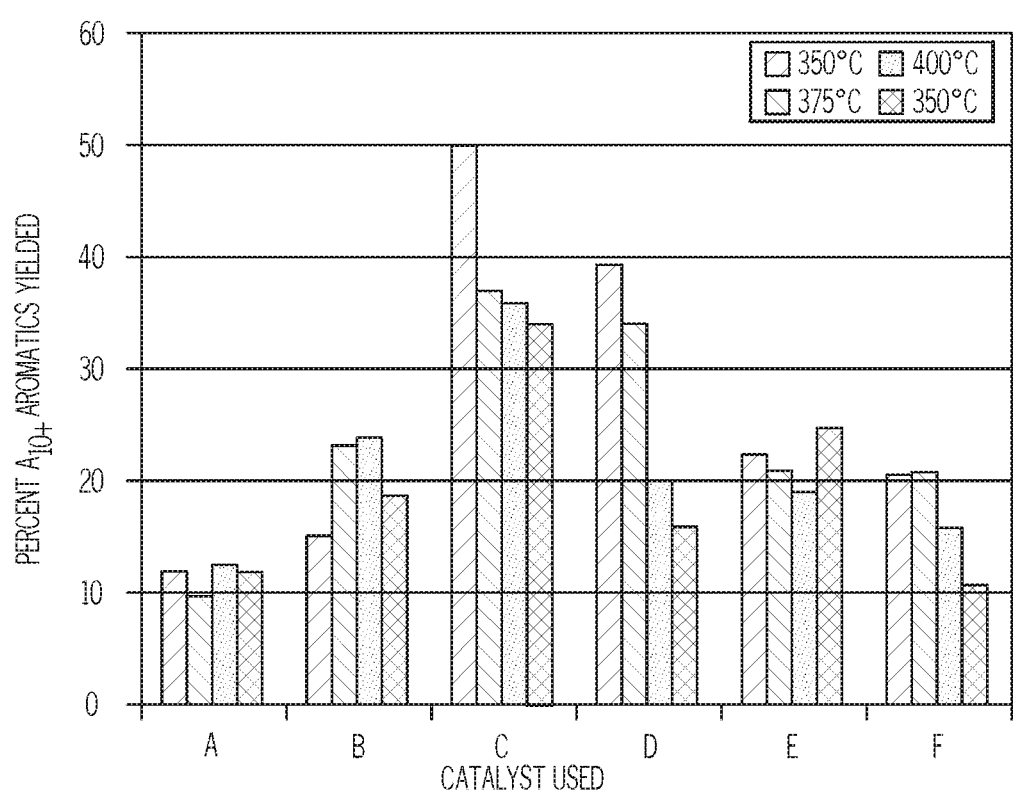
FIG. 9C is a bar chart of the percent of $A_{10+}$ aromatics yielded as a function of temperature when a feed stream reacts with a catalyst; the reaction conditions and catalyst are the same as that described for FIG. 8A supra.

When Re Cat. 4 was combined with the Re ZSM-5, there was an increase in conversion of the MEB as compared to the desilicated mesoporous mordenite, Re Cat. 1 and Re Cat. 4, especially at 350° C. When the desilicated mesoporous mordenite compounds are mixed with ZSM-5 (Re Cat. 4+Re ZSM-5), the TMB conversion and overall conversion was comparable to that of the comparative catalyst, ATA-21, which is also thought to be combined with ZSM-5. However, mixing the desilicated mesoporous mordenite with ZSM-5, reduced the amount of heavy aromatics ($A_{10+}$) produced, as shown in FIGS. 9A-9C. Additionally, the yield to xylenes is maximized. Thus, the combination of mesoporous mordenite with a medium pore zeolite is highly effective for the production of the desired xylenes fraction.

The Re Cat. 4+Re ZSM-5, which included desilicated mesoporous mordenite and ZSM-5, demonstrated greater conversions of TMB and MEB, while producing greater quantities of xylenes at lesser temperatures (350° C. and 375° C.) when compared to Re MOR or Re MOR+Re ZSM-5. Re Cat. 4+Re ZSM-5 had more than 80% conversion of MEB and 39% to 40% conversion of TMB with production of lesser amounts of coke precursors, like greater membered aromatic $C_{10}$ and $C_{11}$ species as shown in FIGS. 9B and 9C.

Controlled generation of mesoporosity in large pore mordenite zeolite, MOR, by acidic treatments and desilication treatments not only improved transalkylation activity and catalyst life of the zeolite catalyst containing the desilicated mesoporous mordenite, but its dealkylation activity. The presence of additional mesoporosity resulted in a more efficient use of the zeolite micropore volume, largely preserved during the desilication treatments, due to the decreased length of the diffusion pathways.

Additionally, high heavy reformate conversions were achieved when the mesopore volume of the mordenite zeolite were increased when combined with dealumination and desilication treatments. The production of heavy aromatics could be controlled by combining the desilicated mesoporous mordenite with ZSM-5, increasing the dealkylation capacity of the catalyst, and therefore maximizing the production of xylenes.

It should be understood that the various aspects of method of making BTX compounds comprising benzene, toluene, and xylene may be utilized in conjunction with various other aspects.

In a first aspect, the disclosure provides a method of making BTX compounds comprising benzene, toluene, and xylene. The method comprises feeding a heavy reformate stream to a reactor, the reactor comprising a composite zeolite catalyst, where the composite zeolite catalyst comprises a mixture of a desilicated mesoporous mordenite and ZSM-5, and the desilicated mesoporous mordenite, the ZSM-5, or both, comprise one or more impregnated metals. The method further includes producing the BTX compounds by simultaneously performing a transalkylation reaction and a dealkylation reaction of the heavy reformate stream in the reactor, where the composite zeolite catalyst is able to catalyze the transalkylation reaction and the dealkylation reaction simultaneously.

In a second aspect, the disclosure provides the method of the first aspect in which the heavy reformate stream comprises at least 15 weight percent (wt. %) methylethylbenzene (MEB) and at least 50 wt. % trimethylbenzene (TMB), based on the total weight of the heavy reformate stream.

In a third aspect, the disclosure provides the method of the first or second aspects in which the one or more impregnated metals are selected from Group VI and Group VII according to IUPAC nomenclature, in which the metal in the zeolite catalyst is from 0.05 to 10 wt. %, based on the total weight of the zeolite catalyst.

In a fourth aspect, the disclosure provides the method of any of the first through third aspects in which the composite zeolite catalyst has a weight ratio of ZSM-5 to desilicated mesoporous mordenite of from greater than 0 to 1.0.

In a fifth aspect, the disclosure provides the method of any of the first through third aspects in which the composite zeolite catalyst comprises a mixture of ZSM-5 and desilicated mesoporous mordenite in a 60:40 to 80:20 weight ratio.

In a sixth aspect, the disclosure provides the method of any of the first through fifth aspects in which the one or more impregnated metals are selected from the group consisting of molybdenum, chromium, nickel, tungsten, palladium, ruthenium, gold, rhenium, rhodium, or combinations thereof and their respective oxides.

In a seventh aspect, the disclosure provides the method of any of the first through sixth aspects in which the desilicated mesoporous mordenite, the ZSM-5, or both the desilicated mesoporous mordenite and ZSM-5 comprise 0.05 wt. % to 10 wt. % of the one or more impregnated metals.

In an eighth aspect, the disclosure provides the method of any of the first through seventh aspects in which the one or more impregnated metals comprise rhenium (Re).

In a ninth aspect, the disclosure provides the method of the eighth aspect in which the desilicated mesoporous mordenite comprises from 0.25 to 0.55 wt. % Re.

In a tenth aspect, the disclosure provides the method of the eighth or ninth aspects in which the ZSM-5 comprises from 0.25 to 0.55 wt. % Re.

In an eleventh aspect, the disclosure provides the method of any of the first through tenth aspects in which the desilicated mesoporous mordenite has a molar Si to Al ratio of at least 5, as measured by Inductive Coupling Plasma Mass Spectrometry (ICP-MS).

In a twelfth aspect, the disclosure provides the method of any of the first through eleventh aspects in which the ZSM-5 has a Si to Al molar ratio of at least 10, as measured by ICP-MS.

In a thirteenth aspect, the disclosure provides the method of any of the first through twelfth aspects in which the desilicated mesoporous mordenite has a micropore to mesopore volumetric ratio of less than 3.0.

In a fourteenth aspect, the disclosure provides the method of any of the first through thirteenth aspects in which the heavy reformate stream comprises at least 30 wt. % MEB or at least 70 wt. % TMB.

In a fifteenth aspect, the disclosure provides the method of any of the first through fourteenth aspects in which the desilicated mesoporous mordenite has a Brunauer-Emmet-Teller (BET) surface area of at least 420 square meters per gram ($m^2/g$), an external surface area of at least 80 $m^2/g$, or both.

It will be apparent to those skilled in the art that modifications and variations can be made to the embodiments described within this description without departing from the spirit and scope of the claimed subject matter. Thus, it is intended that the specification cover the modifications and variations of the various embodiments described, provided such modifications and variations come within the scope of the appended claims and their equivalents.

What is claimed is:

1. A method of making BTX compounds comprising benzene, toluene, and xylene, the method comprising:
feeding a heavy reformate stream to a reactor, the reactor comprising a composite zeolite catalyst,
where the composite zeolite catalyst comprises a mixture of a desilicated mesoporous mordenite in the acid form and ZSM-5,
the desilicated mesoporous mordenite has a molar Si to Al ratio of at least 30, as measured by Inductive Coupling Plasma Mass Spectrometry (ICP-MS),
the desilicated mesoporous mordenite has a surface Si/Al molar ratio greater than 50, as measured by X-ray photoelectron spectroscopy,
the composite zeolite catalyst comprises a mixture of desilicated mesoporous mordenite and ZSM-5 in a 50:50 to 90:10 weight ratio, and
the desilicated mesoporous mordenite, the ZSM-5, or both, comprise one or more impregnated metals; and
producing the BTX compounds by simultaneously performing a transalkylation reaction and a dealkylation reaction of the heavy reformate stream in the reactor, where the composite zeolite catalyst is able to catalyze the transalkylation reaction and the dealkylation reaction simultaneously.

2. The method of claim 1, where the heavy reformate stream comprises at least 15 weight percent (wt. %) methylethylbenzene (MEB) and at least 50 wt. % trimethylbenzene (TMB), based on the total weight of the heavy reformate stream.

3. The method of claim 1, where the one or more impregnated metals are selected from Group VI and Group VII according to IUPAC nomenclature, in which the metal in the zeolite catalyst is from 0.05 to 10 wt. %, based on the total weight of the zeolite catalyst.

4. The method of claim 1, where the composite zeolite catalyst comprises a mixture of desilicated mesoporous mordenite and ZSM-5 in a 60:40 to 80:20 weight ratio.

5. The method of claim 1, where the one or more impregnated metals are selected from the group consisting of molybdenum, chromium, nickel, tungsten, palladium, ruthenium, gold, rhenium, rhodium, or combinations thereof and their respective oxides.

6. The method of claim 1, where the desilicated mesoporous mordenite, the ZSM-5, or both the desilicated mesoporous mordenite and ZSM-5 comprise 0.05 wt. % to 10 wt. % of the one or more impregnated metals.

7. The method of claim 1, where the one or more impregnated metals comprise rhenium (Re).

8. The method of claim 7, where the desilicated mesoporous mordenite comprises from 0.25 to 0.55 wt. % Re, based on the total weight of the zeolite catalyst.

9. The method of claim 7, where the ZSM-5 comprises from 0.25 to 0.55 wt. % Re, based on the total weight of the zeolite catalyst.

10. The method of claim 1, where the ZSM-5 has a Si to Al molar ratio of at least 10, as measured by ICP-MS.

11. The method of claim 1, where the desilicated mesoporous mordenite has a micropore to mesopore volumetric ratio of less than 3.0.

12. The method of claim 1, where the heavy reformate stream comprises at least 30 wt. % MEB or at least 70 wt. % TMB.

13. The method of claim 1, where the desilicated mesoporous mordenite has a Brunauer-Emmet-Teller (BET) surface area of at least 420 square meters per gram ($m^2/g$), an external surface area of at least 80 $m^2/g$, or both.

* * * * *

UNITED STATES PATENT AND TRADEMARK OFFICE
CERTIFICATE OF CORRECTION

PATENT NO. : 10,927,059 B2
APPLICATION NO. : 16/299838
DATED : February 23, 2021
INVENTOR(S) : Veera Venkata Ramakrishna Tammana et al.

Page 1 of 1

It is certified that error appears in the above-identified patent and that said Letters Patent is hereby corrected as shown below:

In the Specification

In Column 17, Line(s) 46, delete "extentextend" and insert --extent--, therefor.

In Column 18, Line(s) 53, delete "(10 mg cm$^2$)" and insert --(10 mg cm$^{-2}$)--, therefor.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*